United States Patent
Pranckevicius et al.

(10) Patent No.: US 9,738,671 B2
(45) Date of Patent: Aug. 22, 2017

(54) CYCLIC BENT ALLENE METAL COMPLEXES

(71) Applicant: THE GOVERNING COUNCIL OF THE UNIVERSITY OF TORONTO, Toronto (CA)

(72) Inventors: Conor Pranckevicius, Toronto (CA); Douglas Wade Stephan, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 0 days.

(21) Appl. No.: 15/312,694

(22) PCT Filed: Apr. 23, 2015

(86) PCT No.: PCT/CA2015/050341
§ 371 (c)(1),
(2) Date: Nov. 21, 2016

(87) PCT Pub. No.: WO2015/179964
PCT Pub. Date: Dec. 3, 2015

(65) Prior Publication Data
US 2017/0137448 A1    May 18, 2017

(30) Foreign Application Priority Data
May 27, 2014    (EP) .................................... 14170031

(51) Int. Cl.
*C07F 15/00* (2006.01)
(52) U.S. Cl.
CPC ................ *C07F 15/0046* (2013.01)
(58) Field of Classification Search
CPC .................... C07F 15/0022; C07F 15/0046
See application file for complete search history.

(56) References Cited

U.S. PATENT DOCUMENTS 8,680,274 B2    3/2014    Bertrand et al.

FOREIGN PATENT DOCUMENTS

| EP | 2614887 A1 | 1/2012 |
|---|---|---|
| WO | 2013159365 A1 | 4/2012 |

OTHER PUBLICATIONS

Pranckevicius et al. "Three-Coordinate, Cyclic Bent Allene Iron Complexes" Organometallics, 2013, vol. 32, No. 9, pp. 2693-2697.*
Chatwin, S.L., "H-X Bond Activation via Hydrogen Transfer to Hydride in Ruthenium N-Heterocyclic Carbene Complexes: Density Functional and Synthetic Studies", Organometallics, 2006, 25, pp. 99-110.
Lee, J.P. "Six-, Five-, and Four-Coordinate Ruthenium (II) Hydride Complexes Supported by N-Heterocyclic Carbene Ligands: Synthesis, Characterization, Fundamental Reactivity, and Catalytic Hydrogenation of Olefins, Aldehydes, and Ketones", Organometallics, 2009, 28, pp. 1758-1775.
Dehope, A., "Grubbs and Hoveyda-Type Ruthenium Complexes Bearing a Cyclic Bent-Allene", Journal of Organometallic Chemistry 696 (2011) pp. 2899-2903.
Fernandez, I., Exocyclic Delocalization at the Expense of Aromaticity in 3,5-bis( —Donor) Substituted Pyrazolium Ions and Corresponding Cyclic Bent Allenes, Journal of the American Chemical Society, 131, pp. 11875-11881.
Lund, C.L. "A Cis-Bis-Mixed-Carbene Ruthenium Hydride Complex: An Olefin-Selective Hydrogenation Catalyst", Organometallics 2012, 31, Department of Chemistry, University of Toronto, Toronto, Ontario, Canada, pp. 802-805.
Lee, H.M., Catalytic Hydrogenation of Alkenes by the Ruthenium-Carbene Complex HRu(Co)Ci(PCy3)(1Mes)=Bis (1,3-((2,4,6-trimethylphenyl)imidazol-2-ylidene), Organometallics, 2001, 20 (4), American Chemical Society, pp. 794-797.
Beach, N.J., "Carbonyl-Amplified Catalyst Performance: Balancing Stability Against Activity for Five-Coordinate Ruthenium Hydride and Hydridocarbonyl Catalysts", Organometallics, 2009, 28 (2), American Chemical Society, pp. 141-447.
Lavallo, V., "Synthesis and Ligand Properties of Stable Five-Membered-Ring Allenes Containing Only Second-Row Elements", vol. 47, Issue 29, Jul. 7, 2008, Wiley Online Library, pp. 5411-5414.
Bagh. B, "Half Sandwich Ruthenium(II) Hydrides: Hydrogenation of Terminal, Internal, Cyclic and Functionalized Olefins", Dalton Translation, 43(41), Nov. 7, 2014, pp. 15638-45.
International Search Report from co-pending Application EP09155811 dated Jul. 15, 2015, 2 pages.

* cited by examiner

*Primary Examiner* — Joseph Kosack

(57) ABSTRACT

The present invention provides stable, cyclic bent allene metal complexes and methods of conducting chemical processes, preferably olefin hydrogenation, comprising contacting an olefin substrate, preferably an unsaturated polymer, with a cyclic bent allene metal complex as described herein, under hydrogenation conditions.

10 Claims, No Drawings

CYCLIC BENT ALLENE METAL COMPLEXES

FIELD OF THE INVENTION

The present invention provides stable, cyclic bent allene metal complexes and methods of conducting chemical processes, preferably olefin hydrogenation, comprising contacting an olefin substrate, preferably an unsaturated polymer, with a cyclic bent allene metal complex as described herein, under hydrogenation conditions.

BACKGROUND OF THE INVENTION

Metal complex catalysts for the hydrogenation of olefins have been disclosed in past years, typically consisting of a transition metal (e.g. Ru, Rh, Os, Ir) which is coordinated with different types of ligands such as phosphine ligands (e.g. $PPh_3$ or $PCy_3$), hydrogen, halides, CO, NO or N-heterocyclic carbenes (NHCs). A typical example for a rhodium-based hydrogenation catalyst is the "Wilkinson catalyst" as shown in formula A.

(A)

Among the above mentioned ligands, N-heterocyclic carbene ligands have gained high popularity in organometallic chemistry. Their high sigma donating ability and steric bulk has proven functional in stabilizing low-coordinate transition metal complexes, and the added electron richness they confer a metal center can be advantageous in the activation of π-acidic substrates.

In Lee, H. M., Smith Jr., D. C., He, Z., Stevens, E. D., Yi, C. S., Nolan, S. P. *Organometallics*, 2001, 20 (4), 794-797 and Beach, N. J., Blacquiere, J. M., Drouin, S. D., Fogg, D. E. *Organometallics*, 2009, 28 (2), 441-447, synthesized mixed NHC-phosphine variants of the type RuHCl(CO)(PR$_3$)(NHC) as shown in formula B are disclosed. It was found that the use of labile phosphines in combination with strongly donating NHCs had a positive effect on rates of catalysis. The document is silent about the use of these complexes for the hydrogenation of nitrile rubbers.

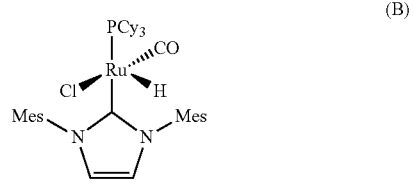

(B)

In Chatwin, S. L., Davidson, M., Doherty, C., Donald, S. M., Jazzar, R., Macgregor, S., McIntyre, G., Mahon, M., Whittlesey, M. *Organometallics* 2006, 25 (1), 99-11, a metal complex with the formula RuHX(CO)(NHC)$_2$ is described as shown in formula C. Lee, J. P., Ke, Z., Ramírez, M. A., Gunnoe, T. B., Cundari, T. R., Boyle, P. D., Petersen, J. L. Organometallics 2009, 28 (6), 1758-1775 discloses the hydrogenation of 1-hexene with the complex of the formula C. However, the catalytic activity is poor compared to [Ru(IMes)$_2$(CO)(H)][BAr'$_4$]. Furthermore, it is not selective for olefins.

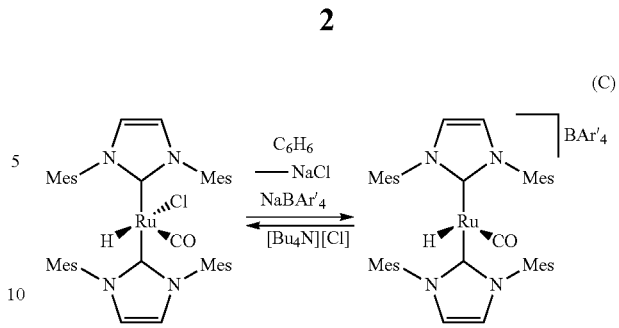

(C)

However, more recently a number of novel divalent carbon species have been synthesized based on other heterocycles such as triazole and pyrazole, offering different electronic characteristics to the classic NHC, many of which have been shown to be more strongly sigma donating.

In Lavallo, V., Dyker, C. A., Donnadieu, B., Bertrand, G. *Synthesis and Ligand Properties of Stable Five-Membered-Ring Allenes Containing Only Second-Row Elements. Angew. Chem. Int. Ed.* 2008, 47, 5411-5414, the synthesis of stable pyrazolin-4-ylidenes that featured heteroatoms at the 3,5 positions of the ring (page 5412, structure 3b), termed "cyclic bent allenes" (CBAs), are reported. It has been shown computationally and experimentally that the introduction of these heteroatoms has a strong influence on the electronic nature of the system, as the ring π-electrons are exocyclically delocalized through these positions. This localizes two lone pairs of electrons on the central carbon atom, making the ligands electronically analogous to carbodicarbenes, part of a growing family of carbon(0) compounds. The isolation of a Rh-biscarbonyl complex as shown in formula D (page 5413, structure 4) bearing this ligand revealed their greater donating power relative to NHCs. However, no mixed CBA/NHC complexes are disclosed. Furthermore, the document is silent about the use of the complex for the hydrogenation of unsaturated olefins.

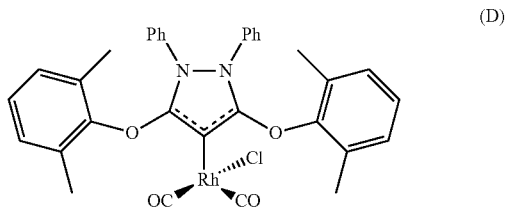

(D)

In Pranckevicius, C., Stephan, D. W. *Three-coordinate, Cyclic Bent Allene Iron Complexes. Organometallics*, 2013, 32, 2693-2697, the preparation of a novel Fe(CBA) complexes as shown in formula E is disclosed. However, the document is silent about the use of these complexes as catalysts for the hydrogenation of olefins.

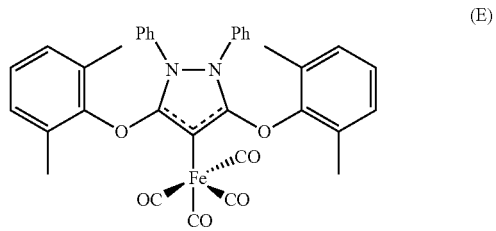

(E)

In DeHope, A., Donnadieu, B., Bertrand, G. *Grubbs and Hoveyda-type ruthenium complexes bearing a cyclic bent-* allene. *Journal of Organometallic Chemistry*, 2011, 696, 2899-2903, a ruthenium-based cyclic bent allene complex is disclosed as shown in formula F (page 2900, complex 3). However, the document discloses only Grubbs and Hoveyda-type ruthenium complexes and is totally silent about the use of these complexes as catalysts for the hydrogenation of unsaturated olefins.

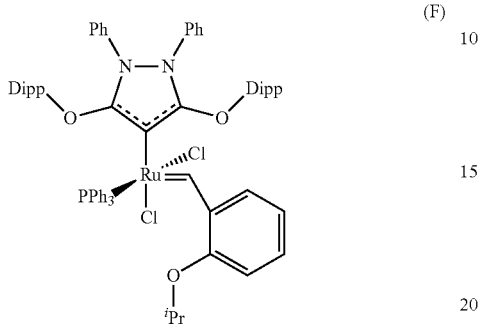

(F)

In WO 2009/089483, bent allene metal complexes are disclosed. According to paragraph [0052], the bent allene can be a 5-membered heterocyclic ring. In paragraph [0057], it is disclosed, that the metal of the bent allene metal complex might be inter alia ruthenium. In paragraph [0060], it is disclosed, that anionic ligands, preferably halides, are suitable as anionic ligands. Hydride as a ligand for the metal complexes is not disclosed in the document. Other suitable ligands can be carbene ligands such as the diaminocarbene ligands (e.g., NHCs). However, paragraph [0060] discloses also the use of phosphines as neutral ligands.

The document discloses in paragraph [0063] the use of bent allene metal complexes as catalysts for a variety of synthetic organic reaction, including amine arylation, Suzuki coupling reactions (aryl-aryl or aryl-alkyl coupling reactions), and α-arylation reactions, hydroformylation (of alkenes and alkynes), hydrosylilation (of alkenes, alkynes, ketones and aldehydes), ring-closing metathesis (RC), ring-opening polymerization metathesis (ROMP), cross metathesis (CM), self-metathesis, acyclic diene metathesis polymerization, ene-yne metathesis, carbonylation, hydroarylation and hydroamination. However, the document is totally silent about the use of these bent allene metal complexes as catalysts for hydrogenation reaction of unsaturated compounds.

The object of the present invention was thus to provide a stable catalyst with excellent activity for the hydrogenation of olefinic compounds, preferable for unsaturated polymers, more preferable for unsaturated nitrile rubbers.

SUMMARY OF THE INVENTION

The above mentioned object has been solved by cyclic bent allene metal complexes of the general formula (I)

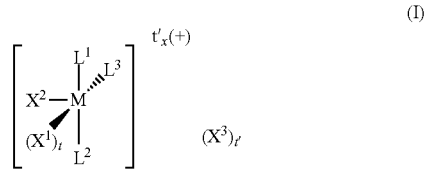

(I)

wherein

M is a transition metal selected from Groups 6-11 of the periodic table, $L^1$ is a cyclic bent allene ligand according to formula (II)

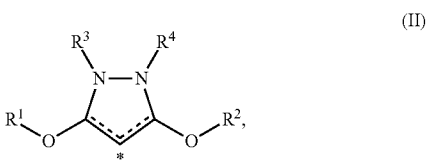

(II)

wherein each of $R^1$, $R^2$, $R^3$ and $R^4$ is independently selected from the group consisting of $C_1$-$C_{10}$-alkyl, $C_3$-$C_{10}$-cycloalkyl, $C_2$-$C_{10}$-alkenyl, $C_3$-$C_{10}$-cycloalkenyl, $C_2$-$C_{10}$-alkynyl, amino, $C_6$-$C_{24}$-aryl, $C_2$-$C_{20}$-heteroaryl, $C_1$-$C_{10}$-heteroalkyl, $C_2$-$C_{10}$-heterocycloalkyl, $C_1$-$C_{10}$-alkoxy, $C_2$-$C_{10}$-alkenyloxy, $C_2$-$C_{10}$-alkynyloxy, halogen, $C_6$-$C_{24}$-aryloxy, $C_2$-$C_{20}$-heteroaryloxy, $C_2$-$C_{10}$-alkoxycarbonyl, $C_1$-$C_{10}$-alkylthio, $C_2$-$C_{10}$-alkenylthio, $C_2$-$C_{10}$-alkynylthio, $C_1$-$C_{10}$-alkylsulfonyl, $C_1$-$C_{10}$-alkylsulfinyl, $C_6$-$C_{24}$-arylsulfonyl, $C_6$-$C_{24}$-aryl-$C_1$-$C_{10}$-alkyl, $C_2$-$C_{20}$-heteroaryl-$C_1$-$C_{10}$-alkyl, $C_6$-$C_{24}$-aryl-$C_1$-$C_{10}$-heteroalkyl, $C_2$-$C_{20}$-heteroaryl-$C_1$-$C_{10}$-heteroalkyl, amido, alkylamino, a phosphorus comprising group, a silicon comprising group and a boron comprising group, and wherein the (\*) indicates the binding site to the transition metal M, $L^2$ is an N-heterocyclic carbene ligand, $L^3$ is a π-acidic donor ligand preferably carbonyl (CO), nitrosyl (NO) or isocyanide, $X^1$ is an anionic ligand, $X^2$ is hydride, $X^3$ is a non-coordinating anion, t is either 0 or 1, and t' is either 0 or 1, wherein t and t' may not both represent 0 at the same time.

DETAILED DESCRIPTION OF THE INVENTION

Abbreviations used herein have their common and accepted meanings to one of skill in the art.

In the present description the term "alkyl", alone or in combination, refers to a straight-chain or branched-chain alkyl group having the indicated number of carbon atoms. For example, $C_1$-$C_{10}$-alkyl refers to an alkyl group having from one to ten carbon atoms with the remaining valences occupied by hydrogen atoms. Preferred alkyl groups are those with 1 to 8 carbon atoms, more preferably a straight or branched-chain alkyl group with 1 to 6 carbon atoms and particularly preferred are straight or branched-chain alkyl groups with 1 to 4 carbon atoms. Examples of straight-chain and branched $C_1$-$C_{10}$-alkyl groups are methyl, ethyl, propyl, isopropyl, butyl, isobutyl, tert-butyl, the isomeric pentyls, the isomeric hexyls, the isomeric heptyls and the like.

The term "cycloalkyl", alone or in combination, refers to a cyclic alkyl group having 3 to 8 carbon atoms as ring vertices. Preferred cycloalkyl groups are those having 3 to 6 carbon atoms. Examples of $C_3$-$C_8$-cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl.

The term "alkenyl", alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of $C_2$-$C_8$-alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "cycloalkenyl", alone or in combination, refers to a cyclic alkenyl group having 3 to 8 carbon atoms as ring vertices. Preferred cycloalkyl groups are those having 3 to 6 carbon atoms. Examples of $C_3$-$C_8$-cycloalkyl are cyclopropenyl, cyclopentenyl dimethylcyclopropenyl and cyclobutyl.

The term "alkoxy", alone or in combination, signifies a group of the formula alkyl-O— in which the term "alkyl" has the previously given definition. It is used in its convention sense, ad refers to those alkyl groups attached to the remainder of the molecule via an oxygen atom. Examples of alkoxy group include methoxy, ethoxy, n-propoxy, iso-propoxy, n-butoxy, iso-butoxy, sec-butoxy and tert-butoxy. Preferred alkoxy groups are methoxy and ethoxy.

The term "alkynyl", alone or in combination refers to a straight-chain or branched hydrocarbon residue having a carbon carbon triple bond and the indicated number of carbon atoms. Preferred alkynyl groups have up to 8, preferably up to 6, particularly preferred up to 4 carbon atoms. Examples of alkynyl groups are ethynyl, 1-propynyl, 1-butynyl and 2-butynyl.

The terms "alkylthio," "alkylsulfonyl," "alkylsulfinyl" and "arylsulfonyl" refer to groups having the formula —S—$R^5$, —S(O)$_2$—$R^5$, —S(O)—$R^5$ and —S(O)$_2R^5$, respectively, in which $R^5$ is an alkyl or $C_6$-$C_{24}$-aryl group as previously defined.

The terms "alkenyloxy" and "alkynyloxy" refer to groups having the formula —O—$R^6$ in which $R^6$ is an alkenyl or alkynyl group, respectively.

The terms "alkenylthio" and "alkynylthio" refer to groups having the formula —S—$R^6$ in which $R^6$ is an alkenyl or alkynyl group, respectively.

The term "alkoxy carbonyl" refers to a group having the formula —C(O)O—$R^5$, wherein $R^5$ is an alkyl group as defined above and wherein the total number of carbon atoms refers to the combined alkyl and carbonyl moieties.

The term "aryl" means, unless otherwise stated, a polyunsaturated, typically aromatic, hydrocarbon group which can be a single ring or multiple rings (up to three rings) which are fused together or linked covalently, preferably $C_6$-$C_{24}$-aryl, more preferably $C_6$-$C_{10}$-aryl, and which optionally carries one or more substituents, preferably halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like. Non-limiting examples of unsubstituted $C_6$-$C_{24}$-aryl groups include phenyl, naphthyl and biphenyl. Examples of substituted $C_6$-$C_{24}$-aryl groups include, but are not limited to, phenyl, chlorophenyl, trifluoromethylphenyl, chlorofluorophenyl and aminophenyl.

The term "heteroalkyl", by itself or in combination with another term, means, unless otherwise stated, a stable straight or branched chain, or combinations thereof, consisting of the stated number of carbon atoms, preferably 1 to 10 carbon atoms, and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "heterocycloalkyl" by itself or in combination with another term refers to a cyclic hydrocarbon radical or a combination of a cyclic hydrocarbon radical with a straight or branched chain alkyl group, consisting of the stated number of carbon atoms, preferably 2 to 10 carbon atoms, and from one to three heteroatoms as ring members selected from the group consisting of O, N, Si and S, and wherein the nitrogen and sulfur atoms may optionally be oxidized and the nitrogen heteroatom may optionally be quaternized. The heterocycloalkyl group is attached to the remainder of the molecule through a carbon atom or a heteroatom.

The term "heteroaryl", alone or in combination, typically signifies aromatic heterocycle which contains one or more, preferably one or two hetero atoms selected from nitrogen, oxygen and sulfur, wherein nitrogen or oxygen are preferred. Preferred heteroaryls are $C_2$-$C_{20}$-heteroaryls with one, two or three heteroatoms. If desired, it can be substituted on one or more carbon atoms substituents, preferably halogen, alkyl, alkoxy, cyano, haloalkyl, preferably trifluoromethyl, and heterocyclyl, preferably morpholinyl or pyrrolidinyl, and the like. Examples of $C_2$-$C_{20}$-heteroaryls include, but are not limited to, pyridinyl or furanyl.

The term "heterocycle", alone or in combination, unless otherwise stated, refers to $C_2$-$C_{20}$-heteroaryl and heterocycloalkyl groups, preferably $C_3$-$C_{10}$-heterocycles.

The term "aryloxy" and "heteroaryloxy", alone or in combination, signifies a group of the formula aryl-O— and heteroaryl-O—, respectively, in which the terms "aryl" and "heteroaryl" have the significance as provided above, preferably phenyloxy, and pyridyloxy, and the like.

The term "amino", alone or in combination, signifies a primary, secondary or tertiary amino group bonded to the remainder of the molecule via the nitrogen atom, with the secondary amino group carrying an alkyl, cycloalkyl, alkenyl, cycloalkenyl, alkynyl, $C_1$-$C_{10}$-heteroalkyl, $C_2$-$C_{10}$-heterocycloalkyl, $C_6$-$C_{24}$-aryl or $C_2$-$C_{20}$-heteroaryl substituent and the tertiary amino group carrying two similar or different alkyl, cycloalkyl, alkenyl, cycloalkenyl, alkynyl, $C_1$-$C_{10}$-heteroalkyl, $C_2$-$C_{10}$-heterocycloalkyl, $C_6$-$C_{24}$-aryl or $C_2$-$C_{20}$-heteroaryl substituents. Alternatively, the two nitrogen substitutents on the tertiary amino group can be taken together to form a 3 to 7 membered ring possibly having to an additional 1 to 2 heteroatoms selected from N, O, P and S as ring vertices. Examples of amino groups include, but are not limited to, —NH$_2$, methylamino, ethylamino, phenylamino, N-phenyl-N-methoxyamino, dimethylamino, diethylamino, methyl-ethylamino, pyrrolidin-1-yl or piperidino etc., preferably amino, dimethylamino and diethylamino.

The term "alkylamino", is used in its conventional sense, and refer to a secondary amino group with an alkyl substituent, and is attached to the remainder of the molecule via the nitrogen atom of the secondary amino group. Additionally, for dialkylamino groups, the alkyl portions can be the same or different and can also be combined to form a 3-7 membered ring with the nitrogen atom to which each is attached. Accordingly, a dialkylamino group is meant to include piperidinyl, pyrrolidinyl, morpholinyl, azetidinyl and the like.

The terms "halo" or "halogen" by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_1$-$C_4$-haloalkyl" is meant to include trifluoromethyl, 2,2,2-trifluoroethyl, 4-chlorobutyl, 3-bromopropyl, and the like.

The term "amido" refers to the group —C(O)NR⁷R⁷ or —NR⁷C(O)R⁷, wherein the R⁷ substituents are independently hydrogen, alkyl, alkenyl or $C_6$-$C_{24}$-aryl.

The term "boron comprising group" as used herein, refers to the group having the general formula —BR⁵R⁵R⁵, wherein R⁵ are independently an alkyl or $C_6$-$C_{24}$-aryl group.

The term "silicon comprising group" as used herein, refers to the group having the general formula —SiR⁷R⁷R⁷, where R⁷ are independently hydrogen, alkyl, alkenyl or $C_6$-$C_{24}$-aryl.

The term "phosphorus comprising group" as used herein, refers to an organic phosphorus group, preferably phosphine, phosphinite, phosphate, phosphonate, phosphate, phosphine oxide, and phosphinate, among others.

The present invention provides cyclic bent allene metal complex of the general formula (I)

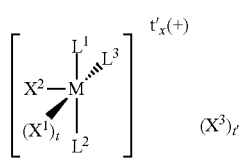

(I)

wherein

M is a transition metal selected from Groups 6-11 of the periodic table,

L¹ is a cyclic bent allene ligand according to formula (II)

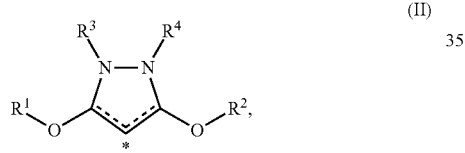

(II)

wherein each of R¹, R², R³ and R⁴ is independently selected from the group consisting of $C_1$-$C_{10}$-alkyl, $C_3$-$C_{10}$-cycloalkyl, $C_2$-$C_{10}$-alkenyl, $C_3$-$C_{10}$-cycloalkenyl, $C_2$-$C_{10}$-alkynyl, amino, $C_6$-$C_{24}$-aryl, $C_2$-$C_{20}$-heteroaryl, $C_1$-$C_{10}$-heteroalkyl, $C_2$-$C_{10}$-heterocycloalkyl, $C_1$-$C_{10}$-alkoxy, $C_2$-$C_{10}$-alkenyloxy, $C_2$-$C_{10}$-alkynyloxy, halogen, aryloxy, $C_2$-$C_{20}$-heteroaryloxy, $C_2$-$C_{10}$-alkoxycarbonyl, $C_1$-$C_{10}$-alkylthio, $C_2$-$C_{10}$-alkenylthio, $C_2$-$C_{10}$-alkynylthio, $C_1$-$C_{10}$-alkylsulfonyl, $C_1$-$C_{10}$-alkylsulfinyl, $C_6$-$C_{24}$-arylsulfonyl, $C_6$-$C_{24}$-aryl-$C_1$-$C_{10}$-alkyl, $C_2$-$C_{20}$-heteroaryl-$C_1$-$C_{10}$-alkyl, $C_6$-$C_{24}$-aryl-$C_1$-$C_{10}$-heteroalkyl, $C_2$-$C_{20}$-heteroaryl-$C_1$-$C_{10}$-heteroalkyl, amido, alkylamino, a phosphorus comprising group, a silicon comprising group and a boron comprising group, and wherein the (*) indicates the binding site to the transition metal M, L² is an N-heterocyclic carbene ligand, L³ is a π-acidic donor ligand, preferably carbonyl (CO), nitrosyl (NO) or isocyanide, X¹ is an anionic ligand, X² is hydride, X³ is a non-coordinating anion, t is either 0 or 1, and t' is either 0 or 1, wherein t and t' may not both represent 0 at the same time.

Definition of Transition Metal

In the complex of the general formula (I), M is a transition metal selected from Groups 6-11 of the periodic table. For example, suitable transition metals include ruthenium, rhodium, palladium, silver, osmium, iridium, platinum, gold, iron, rhenium or nickel.

Preferably, the transition metal is selected from a group consisting of ruthenium, rhodium, palladium, osmium, iridium and platinum.

More preferably, the transition metal is ruthenium or osmium.

Particularly, the transition metal is ruthenium.

Ligand Definition

Definition of L¹ (Cyclic Bent Allene Ligand)

The cyclic bent allene metal complex comprise a cyclic bent allene ligand. As used herein, the term "cyclic bent allene" refers to an allene compound (or ligand) in which the allene portion is made up of three carbon atoms and in which the carbon-carbon-carbon bond angle (typically 180° in linear allenes) has been "bent" to an angle of typically 160° or less. Bending an allene out of a linear configuration is accomplished using substituents that provide a polarization of electrons in the allene. While a single substituent can accomplish a suitable polarization, more typically, a "push-push" of electrons is accomplished with substituents on either end of the allene. When multiple substituents are involved, they can be the same or different and generally provide electron donation to the allene. In this manner, the cyclic bent allene becomes a strong ligand having properties of a carbodianion-type of ligand.

The cyclic bent allene ligand of the present invention is represented by formula (II)

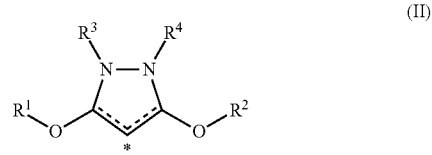

(II)

wherein each of R¹, R², R³ and R⁴ is independently selected from the group consisting of $C_1$-$C_{10}$-alkyl, $C_3$-$C_{10}$-cycloalkyl, $C_2$-$C_{10}$-alkenyl, $C_3$-$C_{10}$-cycloalkenyl, $C_2$-$C_{10}$-alkynyl, amino, $C_6$-$C_{24}$-aryl, $C_2$-$C_{20}$-heteroaryl, $C_1$-$C_{10}$-heteroalkyl, $C_2$-$C_{10}$-heterocycloalkyl, $C_1$-$C_{10}$-alkoxy, $C_2$-$C_{10}$-alkenyloxy, $C_2$-$C_{10}$-alkynyloxy, halogen, $C_6$-$C_{24}$-aryloxy, $C_2$-$C_{20}$-heteroaryloxy, $C_2$-$C_{10}$-alkoxycarbonyl, $C_1$-$C_{10}$-alkylthio, $C_2$-$C_{10}$-alkenylthio, $C_2$-$C_{10}$-alkynylthio, $C_1$-$C_{10}$-alkylsulfonyl, $C_1$-$C_{10}$-alkylsulfinyl, $C_6$-$C_{24}$-arylsulfonyl, $C_6$-$C_{24}$-aryl-$C_1$-$C_{10}$-alkyl, $C_2$-$C_{20}$-heteroaryl-$C_1$-$C_{10}$-alkyl, $C_6$-$C_{24}$-aryl-$C_1$-$C_{10}$-heteroalkyl, $C_2$-$C_{20}$-heteroaryl-$C_1$-$C_{10}$-heteroalkyl, amido, alkylamino, a phosphorus comprising group, a silicon comprising group and a boron comprising group, and wherein the (*) indicates the binding site to the metal M.

Preferably, R¹ and R² of the formula (II) are independently butyl, phenyl, 2,4,6-trimethylphenyl, 2,6-diisopropylphenyl or 2,6-dimethylphenyl and R³ and R⁴ are independently hydrogen, butyl, phenyl, 2,4,6-trimethylphenyl, 2,6-diisopropylphenyl or 2,6-dimethylphenyl.

In a more preferred embodiment, R¹ and R² of the formula (II) are independently butyl, phenyl, 2,4,6-trimethylphenyl, 2,6-diisopropylphenyl or 2,6-dimethylphenyl and R³ and R⁴ are independently hydrogen, butyl or phenyl.

In particular, $R^1$ and $R^2$ of the formula (II) are 2,6-dimethyl-phenyl and $R^3$ and $R^4$ are phenyl.

Additionally, the aliphatic or aromatic portions of $R^1$, $R^2$, $R^3$ and $R^4$ are optionally independently substituted with from 1 to 4 substituents selected from the group consisting of halogen, cyano, nitro, $C_1$-$C_4$-alkyl, $C_2$-$C_6$-alkenyl, $C_2$-$C_6$-alkynyl, $C_6$-$C_{24}$-aryl, $C_1$-$C_6$-alkoxy, $C_2$-$C_6$-alkenyloxy, $C_2$-$C_6$-alkynyloxy, $C_6$-$C_{24}$-aryloxy, $C_2$-$C_6$-alkoxycarbonyl, $C_1$-$C_6$-alkylthio, $C_1$-$C_6$-alkylsulfonyl, $C_1$-$C_6$-alkylsulfinyl, oxo, imino, thiono, primary amino, carboxyl, $C_1$-$C_6$-alkylamino, $C_1$-$C_6$-dialkylamino, amido, nitrogen heterocycles, hydroxy, thiol and phosphorus comprising groups.

Definition of $L^2$ (NHC-ligand)

In the complex of the general formula (I), $L^2$ represents an N-heterocyclic carbene ligand (NHC-ligand).

The NHC-ligand typically represents a cyclic carbene type ligand with at least one nitrogen as hetero atom being present in the ring. The ring can exhibit different substitution patterns on the ring atoms. Preferably this substitution pattern provides a certain degree of steric crowing.

In the context of this invention the N-heterocyclic carbene ligand(s) (hereinafter referred to as "NHC-ligand") is preferably based on imidazoline or imidazolidine moieties.

The NHC-ligand typically has a structure corresponding to the general formulae (IIa) to (IIe)

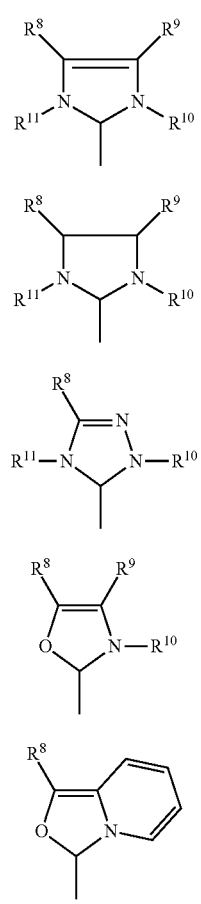

wherein $R^8$, $R^9$, $R^{10}$ and $R^{11}$ are identical or different and represent hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_7$-$C_{25}$-alkaryl, $C_2$-$C_{20}$-heteroaryl, $C_2$-$C_{20}$-heterocyclyl, $C_1$-$C_{20}$-alkoxy, $C_2$-$C_{20}$-alkenyloxy, $C_2$-$C_{20}$-alkynyloxy, $C_6$-$C_{24}$-aryloxy, $C_2$-$C_{20}$-alkoxycarbonyl, $C_1$-$C_{20}$-alkylthio, $C_6$-$C_{24}$-arylthio, —Si(R)$_3$, —O—Si(R)$_3$, —O—C(=O)R, C(=O)R, —C(=O)N(R)$_2$, —NR—C(=O)—N(R)$_2$, —SO$_2$N(R)$_2$, —S(=O)R, —S(=O)$_2$R, —O—S(=O)$_2$R, halogen, nitro or cyano.

If appropriate, one or more of $R^8$, $R^9$, $R^{10}$, and $R^{11}$ can independently of one another, be substituted by one or more substituents, preferably straight-chain or branched $C_1$-$C_{10}$-alkyl, $C_3$-$C_8$-cycloalkyl, $C_1$-$C_{10}$-alkoxy, $C_6$-$C_{24}$-aryl, $C_2$-$C_{20}$-heteroaryl, $C_2$-$C_{20}$-heterocyclic, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein the abovementioned substituents, to the extent chemically possible, may in turn be substituted by one or more substituents, preferably selected from the group consisting of halogen, in particular chlorine or bromine, $C_1$-$C_5$-alkyl, $C_1$-$C_5$-alkoxy and phenyl.

Where the NHC-ligand contains not only an "N" (nitrogen), but also an "O" (oxygen) in the ring it is preferred that the substitution pattern of $R^8$, $R^9$, $R^{10}$ and/or $R^{11}$ provides a certain steric crowding.

In these formulae (IIa) to (IIe) the carbon atom bonding to the ruthenium metal center is formally a carbene carbon.

Merely in the interest of clarity, it may be added that the structures of the NHC-ligand depicted in the general formulae (IIa) and (IIb) in the present patent application are equivalent to the structures (IIa-(i)) and (IIb-(i)) which are frequently also found in the literature for such NHC-ligands, respectively, and emphasize the carbene character of the NHC-ligand. This applies analogously to the associated particularly preferred structures (IIIa)-(IIIu) depicted below.

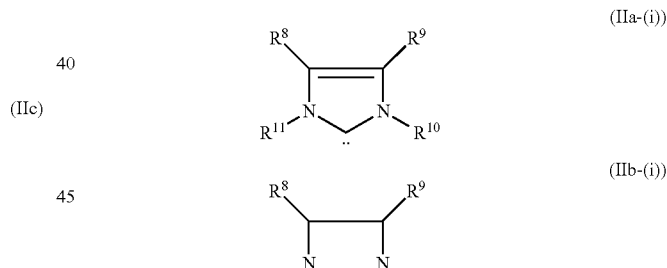

In a preferred NHC-ligand of the complex of the general formula (I)

$R^8$ and $R^9$ are identical or different and represent hydrogen, $C_6$-$C_{24}$-aryl, more preferably phenyl, straight-chain or branched $C_1$-$C_{10}$-alkyl, more preferably methyl, ethyl, n-propyl, iso-propyl, n-butyl, sec-butyl, iso-butyl or tert.-butyl or form a cycloalkyl or aryl structure together with the carbon atoms to which they are bound, and $R^{10}$ and $R^{11}$ are identical or different and preferably represent straight-chain or branched $C_1$-$C_{10}$-alkyl, more preferably iso-propyl or neopentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, or 2,4,6-trimethylphenyl, $C_1$-$C_{10}$-alkylsulfonate, or $C_6$-$C_{24}$-arylsulfonate.

The preferred meanings of $R^8$, $R^9$, $R^{10}$ and $R^{11}$ may be substituted by one or more further substituents selected from the group consisting of straight-chain or branched $C_1$-$C_{10}$-alkyl or $C_1$-$C_{10}$-alkoxy, $C_3$-$C_8$-cycloalkyl, $C_6$-$C_{24}$-aryl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein all these substituents may in turn be substituted by one or more substituents, preferably selected from the group consisting of halogen, in particular chlorine or bromine, $C_1$-$C_5$-alkyl, $C_1$-$C_5$-alkoxy and phenyl.

In a more preferred NHC-ligand of the complex of the general formula (I)

$R^8$ and $R^9$ are identical or different and represent hydrogen, $C_6$-$C_{24}$-aryl, more preferably phenyl, straight-chain or branched $C_1$-$C_{10}$-alkyl, more preferably methyl, ethyl, n-propyl, iso-propyl, n-butyl, sec-butyl, and iso-butyl, or form a cycloalkyl or aryl structure together with the carbon atoms to which they are bound, and $R^{10}$ and $R^{11}$ are identical or different and preferably represent straight-chain or branched $C_1$-$C_{10}$-alkyl, more preferably iso-propyl or neopentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, or 2,4,6-trimethylphenyl, $C_1$-$C_{10}$-alkylsulfonate, or $C_6$-$C_{24}$-arylsulfonate.

A particularly preferred NHC-ligand of the complex of the general formula (I) has one of the following structures (IIIa) to (IIIu), where "Ph" means in each case phenyl, "Bu" means in each case butyl, i.e. either n-butyl, sec.-butyl, iso-butyl or tert.-butyl, "Mes" represents in each case 2,4,6-trimethylphenyl, "Dipp" means in all cases 2,6-diisopropylphenyl and "Dimp" means in each case 2,6-dimethylphenyl:

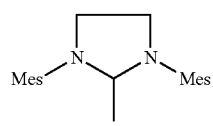
(IIIa)

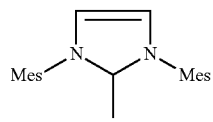
(IIIb)

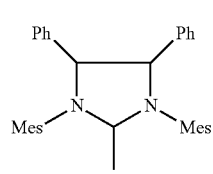
(IIIc)

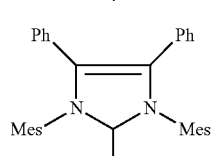
(IIId)

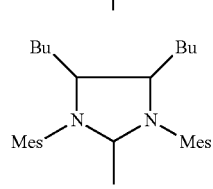
(IIIe)

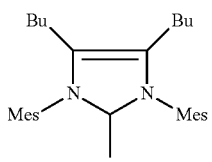
(IIIf)

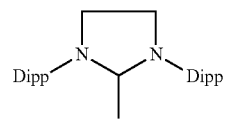
(IIIg)

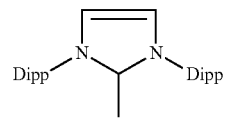
(IIIh)

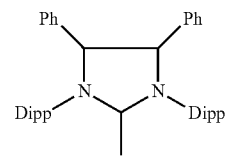
(IIIj)

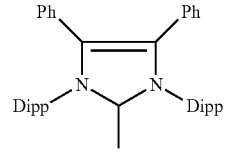
(IIIk)

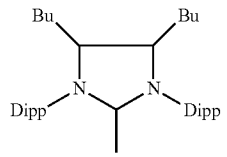
(IIIm)

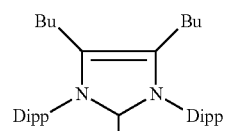
(IIIn)

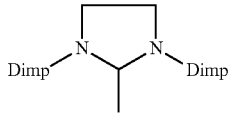
(IIIp)

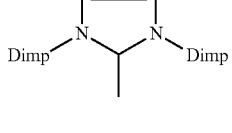
(IIIq)

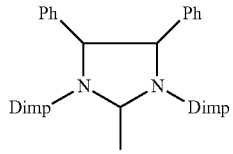
(IIIr)

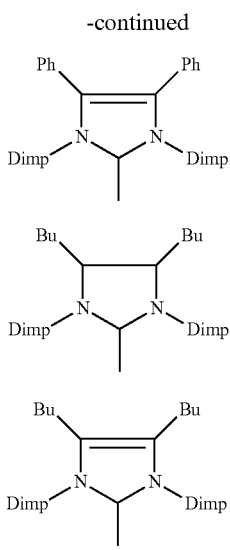

(IIIs)

(IIIt)

(IIIu)

From those particularly preferred NHC-ligands, the most preferred ligands are SIMes (IIIa), IMes (IIIb), IDipp (IIIg), SIDipp (IIIh) and especially SIMes (IIIa).

While the present invention describes a variety of transition metal complexes useful in catalyzing organic reactions, one of skill in the art will appreciate that many of the complexes can be formed in situ. Accordingly, ligands (either cyclic bent allene ligands or additional ligands) can be added to a reaction solution as a separate compound, or can be complexed to the metal center to form a metal-ligand complex prior to its introduction into the reaction solution. The additional ligands are typically compounds added to the reaction solution which can bind to the catalytic metal center. In some preferred embodiments, the additional ligand is a chelating ligand. While the additional ligands can provide stability to the catalytic metal complex, they may also suppress unwanted side reactions as well as enhance the rate and efficiency of the desired processes. Still further, in some embodiments, the additional ligands can prevent precipitation of the catalytic metal complex.

In related embodiments, the present invention provides metal complexes, of the type described above, in which the cyclic bent allene ligand has a pendent functionalized side chain (e.g., aminoalkyl, mercaptoalkyl, acyloxyalkyl and the like) in which the functional group acts as a ligand to provide a bidentate ligand feature.

In still other embodiments, the cyclic bent allene ligand forms a cyclic bent allene metal complex with bidentate ligands that are not tethered to the cyclic bent allene moiety.

Definition of $L^3$ ($\pi$-Acidic Donor Ligand)

In the complex of the general formula (I), $L^3$ represents a $\pi$-acidic donor ligand.

Preferably, the $\pi$-acidic donor ligand is carbonyl (CO), nitrosyl (NO) or isocyanide.

In a more preferred embodiment, the $\pi$-acidic donor ligand is carbonyl (CO) or nitrosyl (NO).

In particular, the $\pi$-acidic donor ligand is carbonyl (CO).

Definition of $X^1$

In the complex of the general formula (I), $X^1$ represents an anionic ligand.

The anionic ligand $X^1$ can be, for example, hydride, halide, pseudohalide, alkoxide, amide, phosphate, borate, carboxylate, acetate, halogenated acetate, halogenated alkylsulfonate like triflate, tosylate or any weakly coordinating anionic ligands. $X^1$ can also be, for example, straight-chain or branched $C_1$-$C_{30}$-alkyl, $C_6$-$C_{24}$-aryl, $C_1$-$C_{20}$-alkoxy, $C_6$-$C_{24}$-aryloxy, $C_3$-$C_{20}$-alkyldiketonate, $C_6$-$C_{24}$-aryldiketonate, $C_1$-$C_{20}$-carboxylate, $C_1$-$C_{20}$-alkylsulfonate, $C_6$-$C_{24}$-arylsulfonate, $C_1$-$C_{20}$-alkylthiol, $C_6$-$C_{24}$-arylthiol, $C_1$-$C_{20}$-alkylsulfonyl or $C_1$-$C_{20}$-alkylsulfinyl.

Preferably, the anionic ligand $X^1$ is hydride, fluorine, chlorine, bromine or iodine, cyanide, thiocyanate, cyanate, isocyanate, isothiocyanate, phosphate, borate, carboxylate, acetate ($CH_3COO$), trifluoroacetate ($CF_3COO$), $CFH_2COO$, $(CH_3)_3CO$, $(CF_3)_2(CH_3)CO$, $(CF_3)(CH_3)_2CO$, trifluormethylsulfonate (abbreviated -OTf; $CF_3SO_3$), tosylate (p-$CH_3$—$C_6H_4$—$SO_3$), mesylate ($CH_3SO_3$) benzoate, $C_1$-$C_5$-carboxylate, $C_1$-$C_5$-alkyl, phenoxy, $C_1$-$C_5$-alkoxy, $C_1$-$C_5$-alkylthiol, $C_6$-$C_{14}$-arylthiol, $C_6$-$C_{14}$-aryl- or $C_1$-$C_5$-alkylsulfonate.

In a more preferred embodiment, the anionic ligand $X^1$ is trifluormethylsulfonate ($CF_3SO_3$) or chloride.

In particular, the anionic ligand $X^1$ is chloride.

Definition of $X^2$

In the complex of the general formula (I), $X^2$ represents hydride.

Preferably, $X^2$ represents hydride.

Definition of $X^3$ $X^3$ represents a non-coordinating anion acting as a counterion. It represents a counterion with a single negative charge or an equivalent thereof. In one embodiment $X^3$ can have the meaning $(ER^{12}_4)^-$ in which E means B, Al, or Ga and $R^{12}$ are identical or different and have the same meaning as defined above for $X^1$. $X^3$ represents e.g. $BF_4^-$, $ClO_4^-$, $[B(3,5-(CF_3)_2C_6H_3)_4]^-$, $B(C_6F_5)_4^-$, $B(CF_3SO_3)_4^-$, $B(R^{13}SO_3)^-$ (with $R^{13}$ represents H, alkyl or $C_6$-$C_{24}$-aryl) and $Al(OC(CF_3)_3)_4^-$. In an alternative embodiment, $X^3$ represents e.g. $PF_6^-$ or $AgBr_2^-$.

One of skill in the art will appreciate that cyclic bent allene metal complexes according to this invention have a variety of geometries (e.g., trigonal, square planar, trigonal bipyramidal and the like) depending on the nature of the transition metal and its oxidation state and other factors including, for example, additional ligands.

In a preferred embodiment, the cyclic bent allene metal complexes of the present invention does not comprise any phosphine ligands, such as triphenylphosphine ($PPh_3$), or tricyclohexylphosphine ($PCy_3$) and their like.

In a preferred embodiment of the general formula (I),

M is a transition metal selected from a group consisting of ruthenium, rhodium, palladium, osmium, iridium and platinum, $L^1$ is a cyclic bent allene ligand represented by formula (II), wherein $R^1$ and $R^2$ of the formula (II) are independently butyl, phenyl, 2,4,6-trimethylphenyl, 2,6-diisopropylphenyl or 2,6-dimethylphenyl and $R^3$ and $R^4$ are independently hydrogen, butyl, phenyl, 2,4,6-trimethylphenyl, 2,6-diisopropylphenyl or 2,6-dimethylphenyl, $L^2$ is an NHC-ligand of the general formula (IIa) to (IIe)

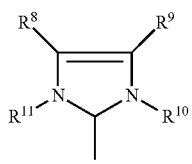

(IIa)

-continued

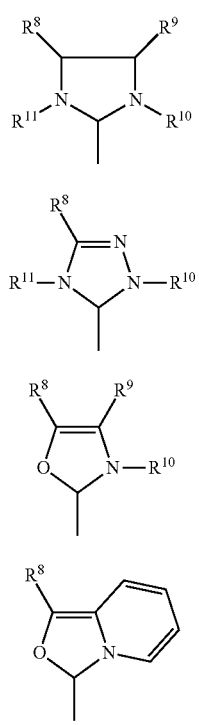

wherein
$R^8$ and $R^9$ are identical or different and represent hydrogen, $C_6$-$C_{24}$-aryl, more preferably phenyl, straight-chain or branched $C_1$-$C_{10}$-alkyl, more preferably methyl, ethyl, n-propyl, iso-propyl, n-butyl, sec-butyl, iso-butyl or tert.-butyl or form a cycloalkyl or aryl structure together with the carbon atoms to which they are bound, and
$R^{10}$ and $R^{11}$ are identical or different and preferably represent straight-chain or branched $C_1$-$C_{10}$-alkyl, more preferably iso-propyl or neopentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, or 2,4,6-trimethylphenyl, $C_1$-$C_{10}$-alkylsulfonate, or $C_6$-$C_{24}$-arylsulfonate,
$L^3$ is carbonyl (CO), nitrosyl (NO) or isocyanide,
$X^1$ is fluorine, chlorine, bromine or iodine, cyanide, thiocyanate, cyanate, isocyanate, isothiocyanate, phosphate, borate, carboxylate, acetate ($CH_3COO$), trifluoroacetate ($CF_3COO$), $CFH_2COO$, $(CH_3)_3CO$, $(CF_3)_2(CH_3)CO$, $(CF_3)(CH_3)_2CO$, trifluormethylsulfonate (abbreviated -OTf; $CF_3SO_3$), tosylate (p-$CH_3$—$C_6H_4$—$SO_3$), mesylate ($CH_3SO_3$) benzoate, $C_1$-$C_5$-carboxylate, $C_1$-$C_5$-alkyl, phenoxy, $C_1$-$C_5$-alkoxy, $C_1$-$C_5$-alkylthiol, $C_6$-$C_{14}$-arylthiol, $C_6$-$C_{24}$-aryl- or $C_1$-$C_5$-alkylsulfonate,
$X^2$ is hydride,
$X^3$, t and t' have the meanings outlined for general formula (I).

In a more preferred embodiment of the general formula (I),
M is ruthenium or osmium,
$L^1$: is a cyclic bent allene ligand represented by formula (II) wherein $R^1$ and $R^2$ of the formula (II) are independently butyl, phenyl, 2,4,6-trimethylphenyl, 2,6-diisopropylphenyl or 2,6-dimethylphenyl and $R^3$ and $R^4$ are independently hydrogen, butyl or phenyl, $L^2$ is an NHC-ligand of the general formula (IIa) to (IIe),

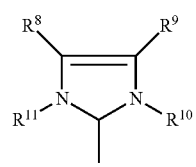

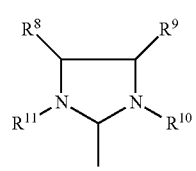

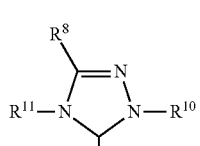

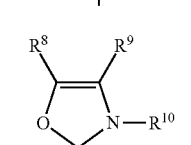

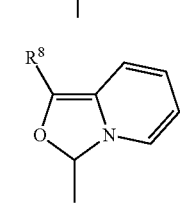

wherein
$R^8$ and $R^9$ are identical or different and represent hydrogen, $C_6$-$C_{24}$-aryl, more preferably phenyl, straight-chain or branched $C_1$-$C_{10}$-alkyl, more preferably methyl, ethyl, n-propyl, iso-propyl, n-butyl, sec-butyl, iso-butyl or tert.-butyl, or form a cycloalkyl or aryl structure together with the carbon atoms to which they are bound, and
$R^{10}$ and $R^{11}$ are identical or different and preferably represent straight-chain or branched $C_1$-$C_{10}$-alkyl, more preferably iso-propyl or neopentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, or 2,4,6-trimethylphenyl, $C_1$-$C_{10}$-alkylsulfonate, or $C_6$-$C_{24}$-arylsulfonate,
$L^3$ is carbonyl (CO) or nitrosyl (NO),
$X^1$ is trifluormethylsulfonate ($CF_3SO_3$) or chloride, and
$X^2$ is hydride,
$X^3$, t and t' have the meanings outlined for general formula (I).

In a particular embodiment of the general formula (I),
M is ruthenium,
$L^1$ is a cyclic bent allene ligand of general formula (II) wherein $R^1$ and $R^2$ of the formula (II) are phenyl and $R^3$ and $R^4$ are 2,6-dimethyl-phenyl, $L^2$ is an NHC-ligand of the general formula (IIa) to (IIe)

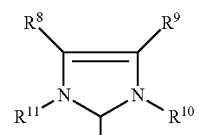
(IIa)

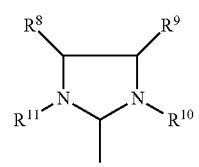
(IIb)

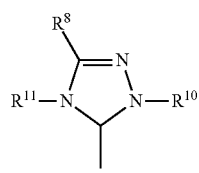
(IIc)

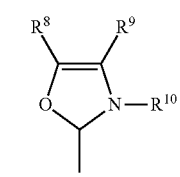
(IId)

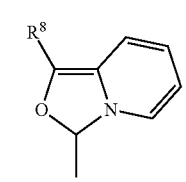
(IIe)

wherein $R^8$ and $R^9$ are hydrogen and $R^{10}$ and $R^{11}$ are 2,4,6-trimethylphenyl (Mes), $L^3$ is carbonyl (CO), $X^1$ is chloride, and $X^2$ is hydride, $X^3$, t and t' have the meanings outlined for general formula (I).

Examples for cyclic bent allene metal complexes according to the definition of the general formula (I) are shown e.g. in the following formulae (I.1) to (I.36):

(I.1)

(I.2) 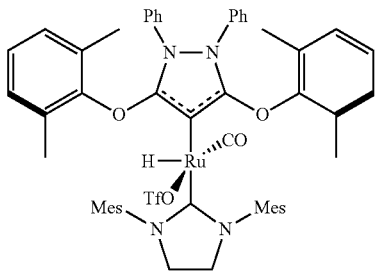

(I.3) 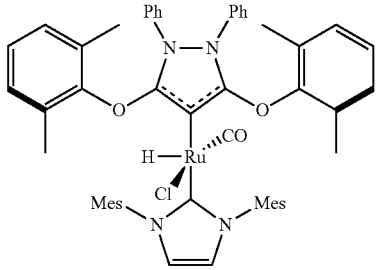

(I.4) 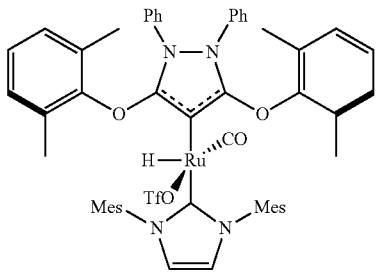

(I.5) 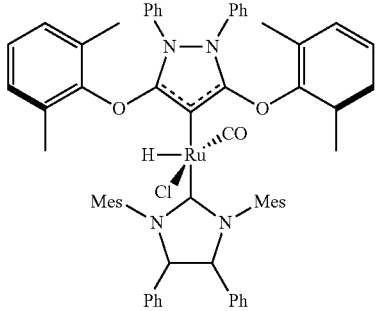

(I.6) 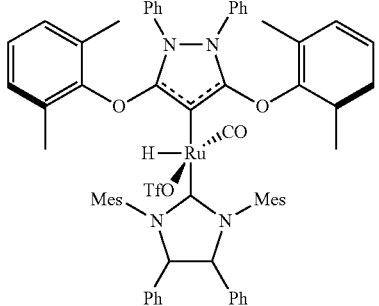

-continued
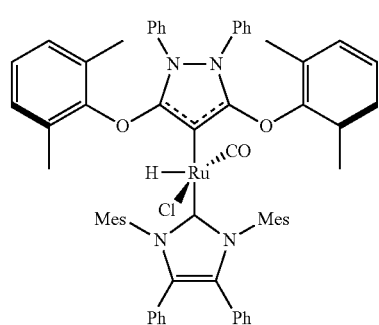 (I.7)
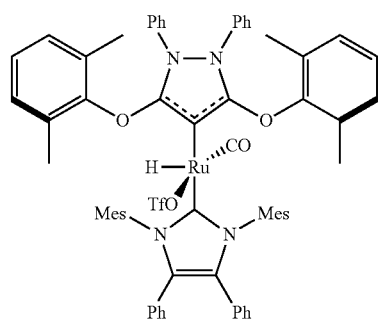 (I.8)
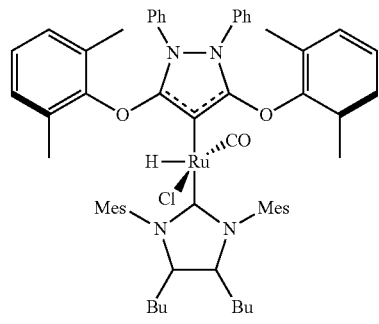 (I.9)
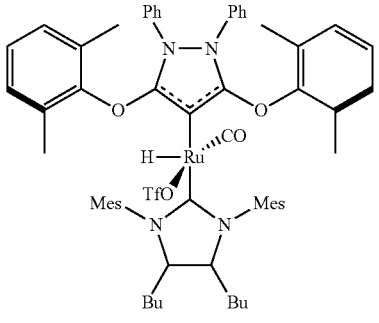 (I.10)
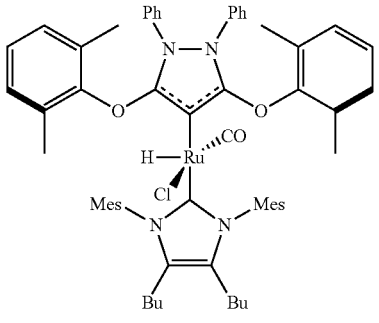 (I.11)
-continued
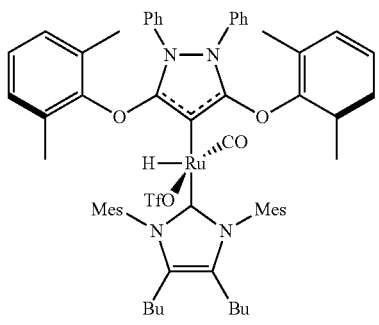 (I.12)
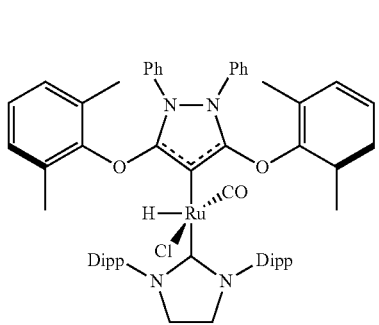 (I.13)
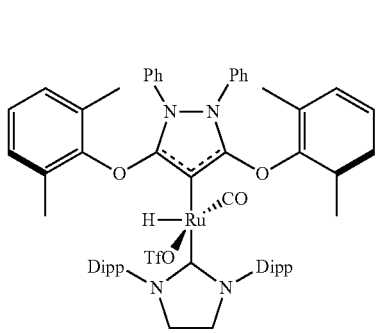 (I.14)
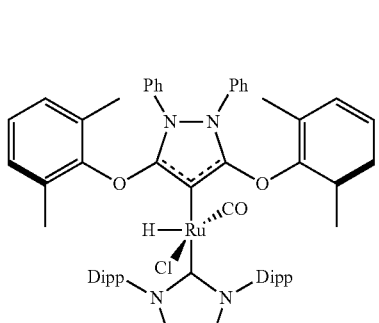 (I.15)
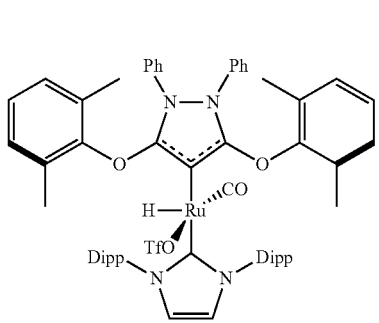 (I.16)

-continued
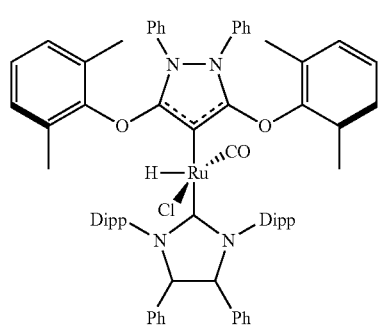
(I.17)
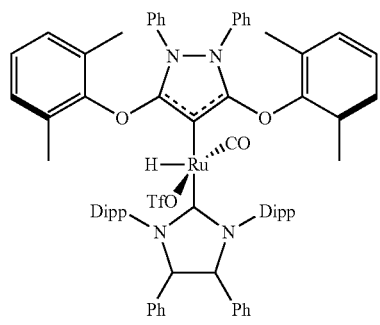
(I.18)
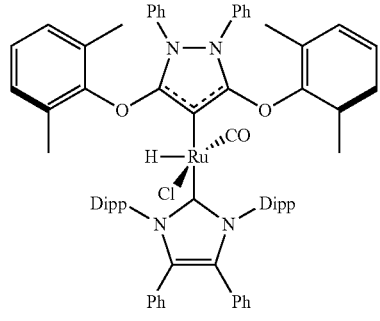
(I.19)
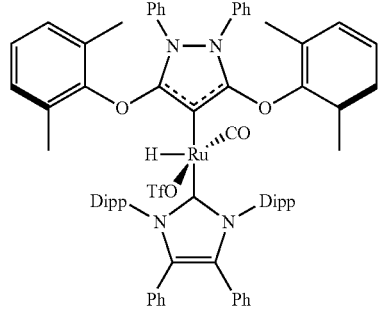
(I.20)
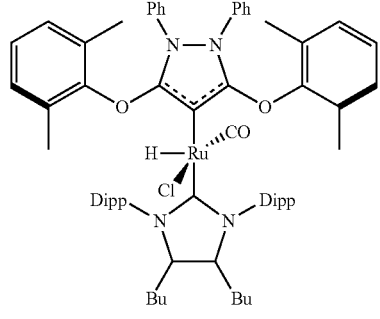
(I.21)
-continued
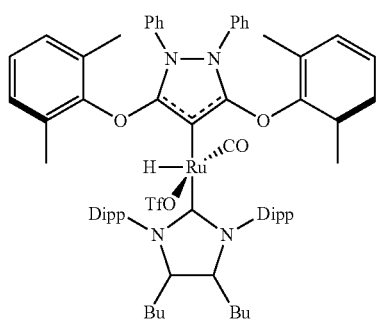
(I.22)
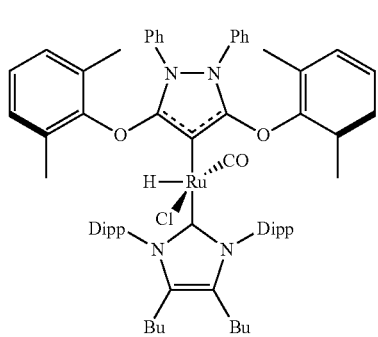
(I.23)
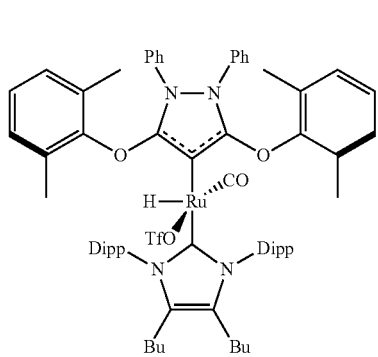
(I.24)
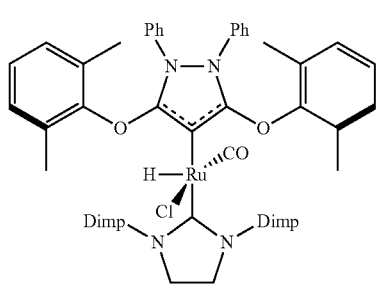
(I.25)
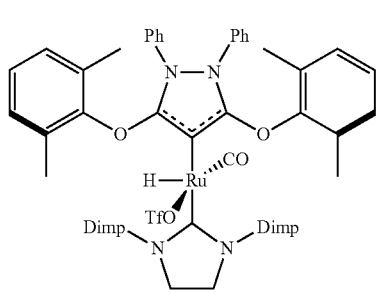
(I.26)

-continued
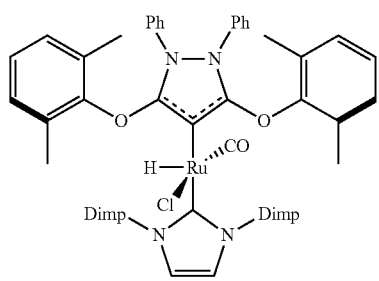 (I.27)
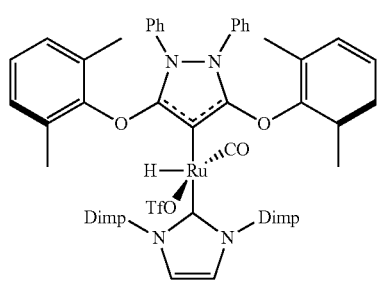 (I.28)
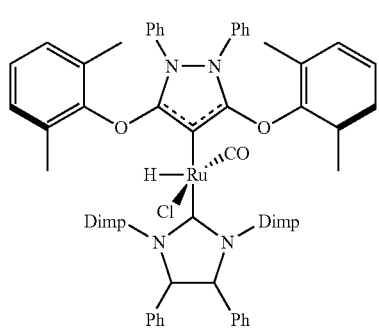 (I.29)
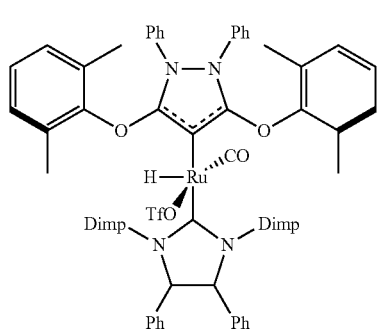 (I.30)
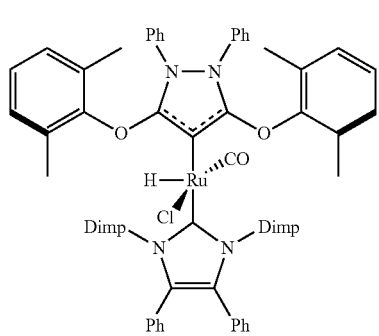 (I.31)
-continued
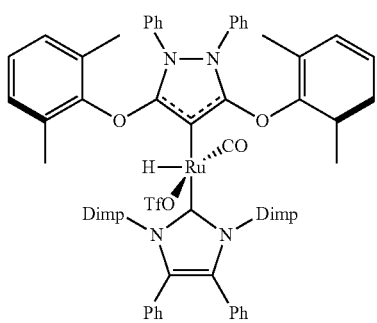 (I.32)
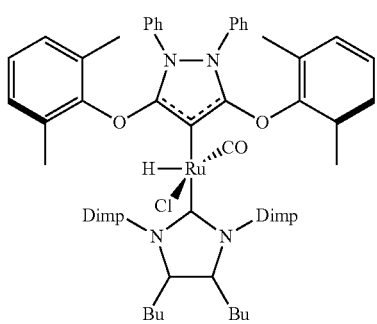 (I.33)
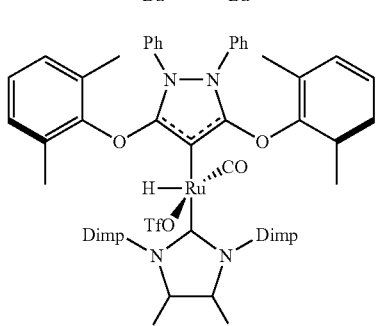 (I.34)
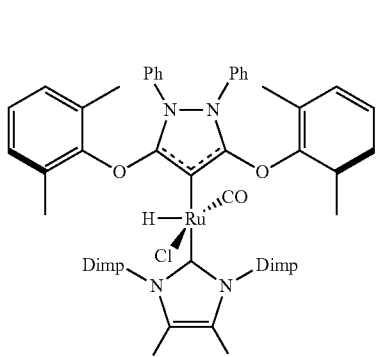 (I.35)
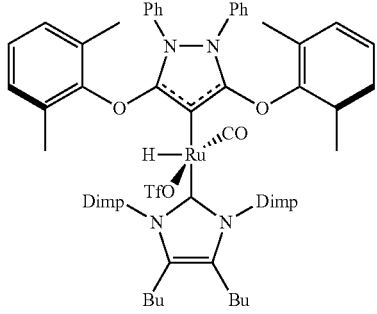 (I.36)

Preparation of Cyclic Bent Allenes and Cyclic Bent Allene Metal Complexes

The present invention resides in the discovery that stable cyclic bent allene metal complexes according to formula (I) can be prepared.

A possible route for the synthesis of cyclic bent allene ligands is disclosed in Fernandez, I., Dyker, A., Dehope, A., Donnadieu, B., Frenking, G., Bertrand, G. *J.A.C.S.* 2009, 131, 11875-11881 and Lavallo, V., Dyker, C. A., Donnadieu, B., Bertrand, G. *Angew. Chem. Int. Ed.* 2008, 47, 5411-5414.

A possible routes for the synthesis of cyclic bent allene metal complexes is disclosed in the examples.

Reactions Catalyzed by Cyclic Bent Allene Metal Complex

The cyclic bent allene metal complex of the present invention are useful in catalyzing a variety of synthetic organic reactions including hydrogenation of olefinic compounds, preferable for unsaturated polymers, more preferable for unsaturated nitrile rubbers.

Process for Hydrogenation of Olefinic Substrates

The present invention relates to a process of hydrogenating olefinic substrates possessing at least one carbon-carbon double bond comprising subjecting said substrate to a hydrogenation reaction in the presence of a complex according to general formula (I).

Substrates to be Hydrogenated

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co- or terpolymers.

As a terminal olefin or alkene, it is possible to hydrogenate a hydrocarbon compound with a terminal unsaturated carbon-carbon double bond having the general formula $C_nH_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula $C_nH_{2n}$. The internal olefin can be a straight-chain or a branched hydrocarbon of any length, preferably 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, preferably cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment $C_4$-$C_6$-conjugated dienes are used. Preference is given to 1,3-butadiene, isoprene, 1-methylbutadiene, 2,3-dimethylbutadiene, piperylene, chloroprene, or mixtures thereof. More preference is given to 1,3-butadiene, isoprene or mixtures thereof. Particular preference is given to 1,3-butadiene.

In an alternative embodiment polymers having carbon-carbon double bonds may be subjected to the hydrogenation process which comprise repeating units of not only at least one conjugated diene as monomer (a) but additionally at least one further copolymerizable monomer (b).

Suitable copolymerizable monomers (b) are olefins, preferably ethylene or propylene.

Suitable monomers (b) are vinylaromatic monomers, preferably styrene, alpha-methyl styrene, o-chlorostyrene or vinyltoluenes, vinylesters of aliphatic or branched $C_1$-$C_{18}$-monocarboxylic acids, preferably vinyl acetate, vinyl propionate, vinyl butyrate, vinyl valerate, vinyl hexanoate, vinyl 2-ethylhexanoate, vinyl decanoate, vinyl laurate and vinyl stearate.

Suitable copolymerizable monomers (b) are esters of ethylenically unsaturated monocarboxylic acids or mono- or diesters of dicarboxylic acids with generally $C_1$-$C_{12}$-alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert.-butanol, n-hexanol, 2-ethylhexanol, or $C_5$-$C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

The inventive process may be further used to hydrogenate nitrile rubbers. Nitrile rubbers ("NBR") represent copolymers or terpolymers containing repeating units of at least one conjugated diene monomer, at least one α,β-unsaturated nitrile monomer as suitable copolymerizable monomer (b) and, if appropriate, one or more further copolymerizable monomers.

The conjugated diene in such nitrile rubbers can be of any nature. Preference is given to using $C_4$-$C_6$-conjugated dienes. Particular preference is given to 1,3-butadiene, isoprene, 2,3-dimethylbutadiene, piperylene or mixtures thereof. In particular, use is preferably made of 1,3-butadiene or isoprene or mixtures thereof. Very particular preference is given to 1,3-butadiene.

As α,β-unsaturated nitrile monomer, it is possible to use any known α,β-unsaturated nitrile, with preference being given to $C_3$-$C_5$-α,β-unsaturated nitriles, preferably acrylonitrile, methacrylonitrile, ethacrylonitrile or mixtures thereof. Particularly preference is given to acrylonitrile.

A particularly preferred nitrile rubber to be subjected to hydrogenation according to the invention is thus a copolymer of acrylonitrile and 1,3-butadiene.

In addition to the conjugated diene and the α,β-unsaturated nitrile, it is possible to use one or more further copolymerizable monomers known to those skilled in the art, e.g. termonomers containing carboxyl groups, like α,β-unsaturated monocarboxylic acids, their esters or amides, α,β-unsaturated dicarboxylic acids, their monoesters or diesters, or their corresponding anhydrides or amides.

As α,β-unsaturated monocarboxylic acids it is possible to use acrylic acid and methacrylic acid.

It is also possible to employ esters of the α,β-unsaturated monocarboxylic acids, preferably their alkyl esters and alkoxyalkyl esters. Preference is given to the alkyl esters, especially $C_1$-$C_{18}$-alkyl esters, of the α,β-unsaturated monocarboxylic acids, Particular preference is given to alkyl esters, especially $C_1$-$C_{18}$-alkyl esters, of acrylic acid or of methacrylic acid, more particularly methyl acrylate, ethyl acrylate, propyl acrylate, n-butyl acrylate, tert-butyl acrylate, 2-ethylhexyl acrylate, n-dodecyl acrylate, methyl methacrylate, ethyl methacrylates, butyl methacrylate and 2-ethylhexyl methacrylate. Also preferred are alkoxyalkyl esters of the α,β-unsaturated monocarboxylic acids, more preferably alkoxyalkyl esters of acrylic acid or of methacrylic acid, more particular $C_2$-$C_{12}$-alkoxyalkyl esters of acrylic acid or of methacrylic acid, very preferably methoxymethyl acrylate, methoxyethyl (meth)acrylate, ethoxyethyl (meth)acrylate and methoxyethyl (meth)acrylate. Use may also be made of mixtures of alkyl esters, preferably those mentioned above, for example, with alkoxyalkyl esters, in the form of those mentioned above, for example. Use may also be made of cyanoalkyl acrylate and cyanoalkyl methacrylates in which the C atom number of the cyanoalkyl group is 2-12, preferably α-cyanoethyl acrylate, β-cyanoethyl acrylate and cyanobutyl methacrylate. Use may also be made of hydroxyalkyl acrylates and hydroxyalkyl methacrylate in which the C atom number of the hydroxyalkyl groups is 1-12, preferably 2-hydroxyethyl acrylate, 2-hydroxyethyl methacrylate and 3-hydroxypropyl acrylate; use may also be made of fluorine-substituted benzyl-group-containing acrylates or methacrylates, preferably fluorobenzyl acrylate, and fluorobenzyl methacrylate. Use may also be made of acrylates and methacrylates containing fluoroalkyl groups, preferably trifluoroethyl acrylate and tetrafluoropropyl methacrylate. Use may also be made of α,β-unsaturated carboxylic esters containing amino groups, preferably dimethylaminomethyl acrylate and diethylaminoethyl acrylate.

As copolymerizable monomers it is possible, furthermore, to use α,β-unsaturated dicarboxylic acids, preferably maleic acid, fumaric acid, crotonic acid, itaconic acid, citraconic acid and mesaconic acid.

Use may be made, furthermore, of α,β-unsaturated dicarboxylic anhydrides, preferably maleic anhydride, itaconic anhydride, citraconic anhydride and mesaconic anhydride.

It is possible, furthermore, to use monoesters or diesters of α,β-unsaturated dicarboxylic acids.

These α,β-unsaturated dicarboxylic monoesters or diesters may be, for example, alkyl esters, preferably $C_1$-$C_{10}$-alkyl, more particularly ethyl, n-propyl, isopropyl, n-butyl, tert.-butyl, n-pentyl or n-hexyl esters, alkoxyalkyl esters, preferably $C_2$-$C_{12}$-alkoxyalkyl, more preferably $C_3$-$C_8$-alkoxyalkyl, hydroxyalkyl, preferably $C_1$-$C_{12}$-hydroxyalkyl, more preferably $C_2$-$C_8$-hydroxyalkyl, cycloalkyl esters, preferably $C_5$-$C_{12}$-cycloalkyl, more preferably $C_6$-$C_{12}$-cycloalkyl, alkylcycloalkyl esters, preferably $C_6$-$C_{12}$-alkylcycloalkyl, more preferably $C_7$-$C_{10}$-alkylcycloalkyl, aryl esters, preferably $C_6$-$C_{14}$-aryl esters, these esters being monoesters or diesters, and it also being possible, in the case of the diesters, for the esters to be mixed esters.

Particularly preferred alkyl esters of α,β-unsaturated monocarboxylic acids are methyl (meth)acrylate, ethyl (meth)acrylate, propyl (meth)acrylate, n-butyl (meth)acrylate, t-butyl (meth)acrylate, hexyl (meth)acrylate, 2-ethylhexyl (meth)acrylate, octyl (meth)acrylate, 2-propyl-heptyl acrylate and lauryl (meth)acrylate. More particularly, n-butyl acrylate is used.

Particularly preferred alkoxyalkyl esters of the α,β-unsaturated monocarboxylic acids are methoxyethyl (meth)acrylate, ethoxyethyl (meth)acrylate and methoxyethyl (meth)acrylate. More particularly, methoxyethyl acrylate is used.

Particularly preferred hydroxyalkyl esters of the α,β-unsaturated monocarboxylic acids are hydroxyethyl (meth)acrylate, hydroxypropyl (meth)acrylate and hydroxybutyl (meth)acrylate.

Other esters of the α,β-unsaturated monocarboxylic acids that are used are additionally, for example, polyethylene glycol (meth)acrylate, polypropylene glycol (meth)acrylate, glycidyl (meth)acrylate, epoxy (meth)acrylate, N-(2-hydroxyethyl)acrylamides, N-(2-hydroxy-methyl)acrylamides and urethane (meth)acrylate.

Examples of α,β-unsaturated dicarboxylic monoesters encompass maleic acid monoalkyl esters, preferably monomethyl maleate, monoethyl maleate, monopropyl maleate and mono-n-butyl maleate;

maleic acid monocycloalkyl esters, preferably monocyclopentyl maleate, monocyclohexyl maleate and monocycloheptyl maleate;

maleic acid monoalkyl cycloalkyl esters, preferably monomethyl cyclopentyl maleate and monoethyl cyclohexyl maleate;

maleic acid monoaryl esters, preferably monophenyl maleate;

maleic acid monobenzyl esters, preferably monobenzyl maleate;

fumaric acid monoalkyl esters, preferably monomethyl fumarate, monoethyl fumarate, monopropyl fumarate and mono-n-butyl fumarate;

fumaric acid monocycloalkyl esters, preferably monocyclopentyl fumarate, monocyclohexyl fumarate and monocycloheptyl fumarate;

fumaric acid monoalkyl cycloalkyl esters, preferably monomethyl cyclopentyl fumarate and monoethyl cyclohexyl fumarate;

fumaric acid monoaryl esters, preferably monophenyl fumarate;

fumaric acid monobenzyl esters, preferably monobenzyl fumarate;

citraconic acid monoalkyl esters, preferably monomethyl citraconate, monoethyl citraconate, monopropyl citraconate and mono-n-butyl citraconate;

citraconic acid monocycloalkyl esters, preferably monocyclopentyl citraconate, monocyclohexyl citraconate and monocycloheptyl citraconate;

citraconic acid monoalkyl cycloalkyl esters, preferably monomethyl cyclopentyl citraconate and monoethyl cyclohexyl citraconate;

citraconic acid monoaryl esters, preferably monophenyl citraconate;

citraconic acid monobenzyl esters, preferably monobenzyl citraconate;

itaconic acid monoalkyl esters, preferably monomethyl itaconate, monoethyl itaconate, monopropyl itaconate and mono-n-butyl itaconate;

itaconic acid monocycloalkyl esters, preferably monocyclopentyl itaconate, monocyclohexyl itaconate and monocycloheptyl itaconate;

itaconic acid monoalkyl cycloalkyl esters, preferably monomethyl cyclopentyl itaconate and monoethyl cyclohexyl itaconate;

itaconic acid monoaryl esters, preferably monophenyl itaconate;

itaconic acid monobenzyl esters, preferably monobenzyl itaconate;

mesaconic acid monoalkyl esters, preferably mesaconic acid monoethyl esters.

As α,β-unsaturated dicarboxylic diesters it is possible to use the analogous diesters based on the abovementioned monoester groups, and the ester groups may also be chemically different groups.

Preferably the terpolymer to be hydrogenated is a nitrile rubber comprising repeating units of at least one conjugated diene selected from the group consisting of 1,3-butadiene, isoprene, 2,3-dimethylbutadiene, piperylene and mixtures thereof, at least one α,β-unsaturated nitrile selected from the group consisting of acrylonitrile, methacrylonitrile, ethacrylonitrile and mixtures thereof, and optionally of one or more further copolymerizable monomers selected from the group consisting of α,β-unsaturated monocarboxylic, dicarboxylic acids, their esters or amides.

The proportions of conjugated diene and α,β-unsaturated nitrile monomer in the NBR polymers to be used can vary within wide ranges. The proportion of the conjugated diene or the sum of conjugated dienes is usually in the range from 40 to 90% by weight, preferably in the range from 50 to 85% by weight, based on the total polymer. The proportion of the α,β-unsaturated nitrile or the sum of the α,β-unsaturated nitriles is usually from 10 to 60% by weight, preferably from 15 to 50% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the α,β-unsaturated nitrile or nitriles are replaced by the proportions of the additional monomers, with the proportions of all monomers in each case adding up to 100% by weight.

The preparation of such nitrile rubbers by polymerization of the abovementioned monomers is adequately known to those skilled in the art and is comprehensively described in the literature (e.g. Houben-Weyl, *Methoden der Organischen Chemie Bd.* 14/1, 30 Georg Thieme Verlag Stuttgart 1961; *Römpp Lexikon der Chemie*, Band 2, 10. Auflage 1997; P. A. Lovell, M. S. El-Aasser, *Emulsion Polymerization and Emulsion Polymers*, John Wiley & Sons, ISBN: 047196746 7; H. Gerrens, Fortschr. *Hochpolym. Forsch.* 1, 234 (1959)).

Nitrile rubbers which can be used for the purposes of the invention are commercially available, e.g. as products marketed under the trademarks Perbunan® and Krynac® by Lanxess Deutschland GmbH.

The nitrile rubbers which can be used for the hydrogenation have a Mooney viscosity (ML 1+4 at 100° C.) in the range from 30 to 70, preferably from 30 to 50. This corresponds to a weight average molecular weight Mw in the range 150 000 to 500 000, preferably in the range 180 000 to 400 000. The nitrile rubbers used typically have a polydispersity PDI=Mw/Mn (Mn is the number average molecular weight) in the range of 2.0 to 6.0 and preferably in the range 2.0 to 4.0.

Hydrogenated nitrile rubbers obtained pursuant to this invention can have a Mooney viscosity (ML 1+4 at 100° C.) in the range of greater than 0 up to 150, typically the Mooney viscosity lies in the range of from 5 to 150, preferably of from 10 to 120, more preferably of from 30 to 110, even more preferably of from 35 to 100, and particularly preferably of from 50 to 100 and most preferably of from 60 to 90. The determination of the Mooney viscosity is carried out in accordance with ASTM standard D 1646.

They typically have a polydispersity PDI=Mw/Mn, where Mw is the weight average molecular weight and Mn is the number average molecular weight, in the range of 1.5 to 6 and preferably in the range of 1.8 to 4.

Hydrogenation Conditions:

The hydrogenation process of the present invention can be performed under a wide range of conditions, and the solvents and temperature ranges recited herein should not be considered limiting. In general, it is desirable for the hydrogenation process to be run using mild conditions which will not adversely affect the reactants, the cyclic bent allene metal complex, or the product. For example, the hydrogenation process temperature influences the speed of the hydrogenation process, as well as the stability of the reactants and cyclic bent allene metal complex.

The hydrogenation process of the present invention is generally carried out at a temperature in the range from 0° C. to 200° C., preferably in the range from 15° C. to 150° C. This means that the process may be carried out at mild conditions. In case low molecular weight olefins like terminal olefins, internal olefins, cyclic olefins, conjugated olefins, or any other olefins having at least one carbon-carbon double bond and additionally at least one further polar unsaturated double bond are subjected to hydrogenation, the temperature typically lies in the range from 20° C. to 100° C. In case polymers with double bonds in the polymer backbone are used as substrates the hydrogenation temperature typically lies in a range from 40° C. to 200° C., preferably in the range from 70° C. to 150° C.

The hydrogenation process of the present invention is preferably carried out with hydrogen gas at a pressure from 0.1 MPa to 20 MPa, preferably at a pressure from 1 MPa to 16 MPa. In one embodiment of the present process said hydrogen gas is essentially pure.

Preferably the hydrogenation process is carried out at a temperature in the range from 0° C. to 200° C. with hydrogen gas at a pressure from 0.1 MPa to 20 MPa, preferably at a temperature in the range from 15° C. to 150° C. with hydrogen gas at a pressure from 1 MPa to 16 MPa.

Additionally, the hydrogenation process will typically be run for a time period of from 30 seconds to 100 hours, preferably to 24 hours, depending on other hydrogenation process conditions (e.g. solvent, concentration and amount of cyclic bent allene metal complex).

The amount of complex according to general formula (I) can vary in a broad range. Typically, the complex according to general formula (I) is used in a molar ratio from (0.0000001-0.05):1, preferably from (0.000001-0.001):1 based on the substrate to be hydrogenated.

Typically, the amount of cyclic bent allene metal complex according to general formula (I) used for the hydrogenation of low molecular weight olefins will be from 0.00001 to 5 mol percent, with 0.0001 to 0.1 mol percent being preferred and with 0.005 to 0.1 mol percent being more preferred.

In the hydrogenation of rubber polymers the amount of complex according to formula (I) may also vary in a broad range. The amount of complex is then calculated on a weight base ratio in "phr" (parts per hundred rubber). Typically 0.000001 phr to 0.5 phr complex are used based on the rubber, preferably 0.000001 phr to 0.05 phr complex are used based on the rubber.

The hydrogenation process are generally carried out in a liquid reaction medium, but in some instances can be run without addition of solvent. For those hydrogenation process conducted in solvent, an inert solvent is preferred, particularly one in which the hydrogenation process ingredients, including the cyclic bent allene metal complex, are substantially soluble and which does not deactivate the complex used and also does not adversely affect the hydrogenation process in any other way. Preferred solvents include but are not restricted to methanol, chlorobenzene, bromobenzene, dichloromethane, dichloroethane, benzene, xylene, toluene, hexane, pentane, methyl ethyl ketone, acetone, tetrahydrofuran (THF), tetrahydropyran, 2-butanone, dioxane and cyclohexane. The particularly preferred solvent is chlorobenzene. In some cases, when the substrate to be hydrogenated itself can function as solvent, e.g. in the case of 1-hexene, the addition of a further additional solvent can also be omitted.

According to the present invention the complex can be introduced into the polymer by any possible means, such as e.g. mechanical mixing, preferably by using a procedure which can result in a homogeneous distribution of the complex and polymer.

In one embodiment of the present invention the complex according to formula (I) is contacted with the substrate to be hydrogenated by adding the complex or complex solution to a substrate solution and mixing until an efficient distribution and dissolution of the complex has taken place.

The present process can be performed in the presence or absence of any further co-catalyst or other additives. It is not necessary to add such further co-catalyst or other additives.

The hydrogenation process of the present invention can be undertaken in a suitable reactor equipped with temperature regulating and agitating means. It is possible to perform the process either batch-wise or continuously.

In some embodiments, the hydrogenation process utilizing the cyclic bent allene metal complex of the present invention can be run in a biphasic mixture of solvents, in an emulsion or suspension, or in a lipid vesicle or bilayer. In certain embodiments, the catalyzed hydrogenation process can be run in the solid phase with one of the reactants tethered or anchored to a solid support.

During the course of the hydrogenation process of the present invention, the hydrogen is added to the reactor. As the novel complex are stable and robust, it is typically not necessary to use a special gas dryer to dry the hydrogen.

In certain embodiments it is preferable to perform the hydrogenation process under an inert atmosphere of a gas, preferably nitrogen or argon.

The hydrogenation process of the present invention can be conducted in continuous, semi-continuous or batch fashion and may involve a liquid recycle operation as desired. The processes of this invention are preferably conducted in batch fashion. Likewise, the manner or order of addition of the reaction ingredients, complex and solvent are also not generally critical to the success of the hydrogenation process, and may be accomplished in any conventional fashion.

The hydrogenation process can be conducted in a single reaction zone or in a plurality of reaction zones, in series or in parallel or it may be conducted batchwise or continuously in an elongated tubular zone or series of such zones. The materials of construction employed should be inert to the starting materials during the hydrogenation process and the fabrication of the equipment should be able to withstand the hydrogenation process temperatures and pressures. Means to introduce and/or adjust the quantity of starting materials or ingredients introduced batchwise or continuously into the reaction zone during the course of the hydrogenation process can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal complex. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" hydrogenation process temperatures.

Furthermore, one or more of the reactants can be immobilized or incorporated into a polymer or other insoluble matrix by, for example, derivatization with one or more of substituents of the aryl group.

According to the present invention, when the hydrogenation process is complete, to the extent desired, the reaction vessel can be cooled (if applicable) and vented and the hydrogenated substrate can be isolated by conventional methods well known to any artisan.

During the process according to the invention it may happen that a hydrogenation process and a metathesis reaction occur simultaneously. In case polymeric substrates and in particular nitrile rubbers are used as substrates in the process according to the invention, such metathesis reaction results in a decrease of the molecular weight of the substrate.

The novel cyclic bent allene metal complexes can be used as catalysts for the hydrogenation of unsaturated compounds comprising carbon-carbon double bonds, preferably nitrile rubber.

EXAMPLES

General Remarks:

All manipulations were carried out under an atmosphere of dry, $O_2$-free $N_2$ employing a Vacuum Atmospheres glovebox or a Schlenk vacuum line. Solvents were purified with a Grubbs-type column system manufactured by Innovative Technology and dispensed into thick-walled Straus flasks equipped with Teflon-valve stopcocks. Deuterated dichloromethane was distilled under reduced pressure from $CaH_2$ and degassed by successive freeze-pump-thaw cycles. Deuterated benzene was distilled from purple sodium benzophenone ketyl.

$^1H$, $^{13}C$, $^{31}P$ and $^{19}F$-NMR spectra were recorded at 25° C. on Bruker 400 MHz spectrometers, unless otherwise noted. Chemical shifts are reported in parts per million (ppm) are given relative to $SiMe_4$ and referenced to the residual solvent signal.

Combustion analyses were performed employing a Perkin-Elmer 2400 Series II CHN Analyzer.

IR spectra were collected on a Perkin-Elmer Spectrum One FT-IR instrument.

Gas chromatography (GC): was performed with an Agilent Technologies GCMS incorporating a 7890A GC System and a 5975C VLMSD with Triple Axis Detector.

$RuHCl(CO)(PPh_3)_3$ and $Me_3SiOSO_2CF_3$ were purchased from Strem and used without subsequent purification.

Synthesis of Cyclic Bent Allene 1,2-Diphenyl-3,5-bis(2,6-dimethylphenoxy)-pyrazolin-4-ylidine $(C_6H_3Me_2O)_2C_3(NPh)_2$ Finely powdered 1,2-diphenyl-3,5-(2,6-dimethylphenoxy)pyrazolium tetrafluoroborate (800 mg, 1.46 mmol)

was combined with potassium hexamethyldisilazide (292 mg, 1.46 mmol), and the mixture was cooled to −47° C. Diethyl ether (10 mL) was added at this temperature, and the stirred mixture was warmed to room temperature over the course of 50 min. Diethyl ether (15 mL) was then added, and the resultant suspension was filtered through a fine-porosity glass frit. The solution was concentrated under high vacuum until light yellow crystals just began to form (approximately 5 mL), and pentane (10 mL) was added. The solution was reconcentrated to 5 mL, resulting in the precipitation of a large crop of light yellow crystals. This process was repeated once more to effect complete precipitation of the product. The remaining supernatant was decanted, and the light yellow precipitate was washed with pentane (2×10 mL) and dried under high vacuum (525 mg, 88%).

Synthesis of Cyclic Bent Allene Metal Complex 1—Ru(CBA)(PPh$_3$)$_2$(CO)HCl

Direct metallation of Ru:

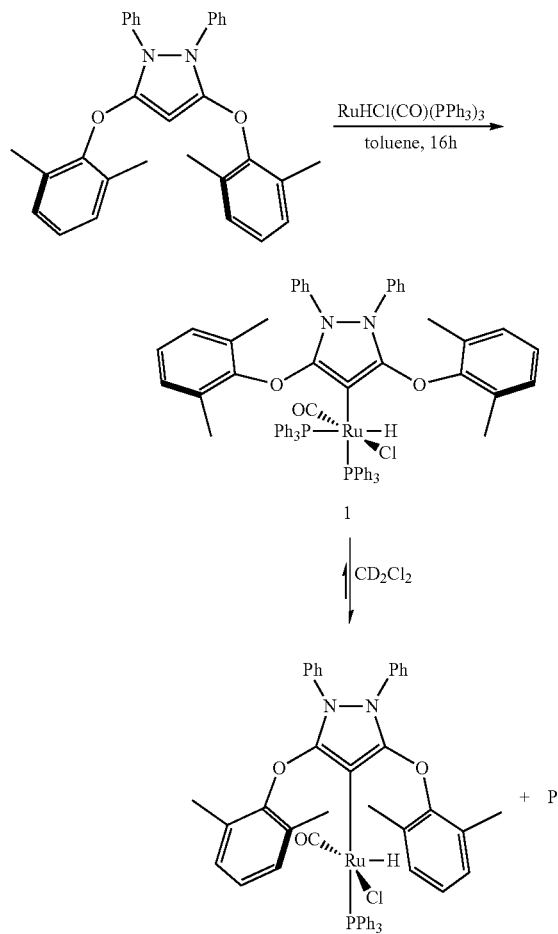

The cyclic bent allene (271 mg, 0.588 mmol) was added to a suspension of Ru(PPh$_3$)$_3$(CO)HCl (504 mg, 0.529 mmol) in toluene (10 mL) and the mixture was stirred overnight (16 hours). The suspension was then filtered through a plug of celite and the solvent was removed under vacuum without stirring, causing X-ray quality crystals of the product to precipitate in a red-brown oil. The mixture was triturated with small successive portions of diethyl ether until the supernatant became pale yellow in color. The crystalline beige solid obtained was further washed with pentane (2×5 mL) and dried under high vacuum (289 mg, 47%). No NMR data could be obtained as the complex readily dissociates triphenylphosphine in solution, forming cyclic bent allene metal complex 2.

IR(KBr): 1899 cm$^{-1}$ (vCO).

Anal. Calcd. for C$_{50}$H$_{44}$ClN$_2$O$_3$PRu (1150.67): C, 70.98; H, 5.17; N, 2.43. Found: C, 71.24; H, 5.15; N, 2.45.

Synthesis of Cyclic Bent Allene Metal Complex 2—Ru(CBA)(PPh$_3$)(CO)HCl

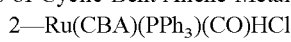

Phosphine loss:

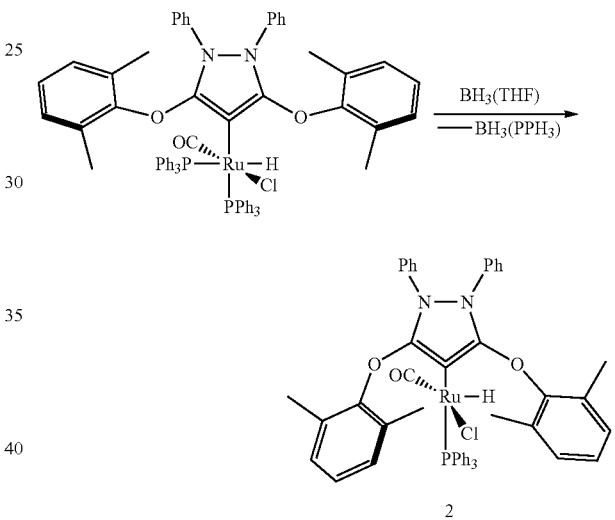

To a solution of 1 (168 mg, 0.146 mmol) in THF (5 mL) BH$_3$ (1.0 M in THF, 146 µL, 0.146 mmol) was added. The solution was concentrated to approximately 1 mL and pentane (15 mL) was added to precipitate the product. The bright yellow solid was collected by filtration and dried under high vacuum (121 mg, 93%).

$^1$H-NMR (CD$_2$Cl$_2$): 7.49 (d, $^3J_{H\text{-}H}$=8.0 Hz, 4H, o-Ph), 7.42 (t, $^3J_{H\text{-}H}$=8.0 Hz, 4H, m-Ph), 7.37-7.21 (m, 17H, PPh$_3$ & p-Ph), 7.01 (br s, 2H, m-OAr), 6.74 (br s, 2H, m-OAr), 6.44 (br s, 2H, p-OAr), 2.28 (br s, 6H, OArCH$_3$), 2.09 (br s, 6H, OArCH$_3$), −24.21 (d, $^2J_{H\text{-}P}$=26.3 Hz, 1H, RuH).

$^{13}$C-NMR (CD$_2$Cl$_2$): 136.92 (d, $^1J_{C\text{-}P}$=36.4 Hz, ipso-PPh$_3$), 134.96, 134.66 (d, $^3J_{C\text{-}P}$=11.3 Hz, o-PPh$_3$), 129.84, 129.17 (d, $^4J_{C\text{-}P}$=10.0 Hz, m-PPh$_3$), 129.10, 127.67 (d, $^5J_{C\text{-}P}$=9.1 Hz, p-PPh$_3$), 126.68, 125.93, 17.53 (br, CH$_3$).

$^{31}$P-NMR(CD$_2$Cl$_2$): 44.60 (d, $^2J_{H\text{-}P}$=23.5 Hz, PPh$_3$).

IR(KBr): 1892 cm$^{-1}$ (vCO).

Anal. Calcd. for C$_{50}$H$_{44}$ClN$_2$O$_3$PRu (888.39): C, 67.60; H, 4.99; N, 3.15. Found: C, 67.87; H, 5.34; N, 2.93.

Synthesis of Cyclic Bent Allene Metal Complex 3—Ru(CBA)(SIMes)(CO)HCl

SIMes substitution:

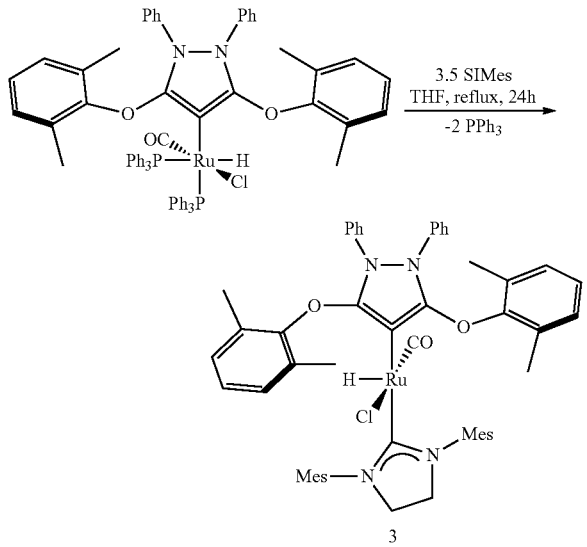

To a solution of 1 (150 mg, 0.130 mmol) in THF (5 mL) was added SIMes (140 mg, 0.457 mmol) and the solution was re-fluxed for 24 hours. The solution was cooled to room temperature and concentrated to approximately 1 mL. Pentane (15 mL) was added to precipitate the product as a bright yellow-orange solid, which was washed with pentane (3×10 mL) and dried under high vacuum (111 mg, 92%).

$^1$H-NMR (C$_6$D$_6$): 6.88 (br s, 2H, Mes), 6.86-6.77 (m, 6H), 6.75 (d, $^3J_{H-H}$=8.0 Hz, 4H, m-OAr), 6.65 (br s, 2H, Mes), 6.60-6.57 (m, 6H), 3.30 (m, 4H, NCH$_2$CH$_2$N), 2.73 (br s, MesCH$_3$, 6H), 2.51 (br s, MesCH$_3$, 6H), 2.15 (br s, OArCH$_3$, 12H), 2.05 (br s, MesCH$_3$, 6H), −26.04 (s, 1H, Ru—H).

$^{13}$C-NMR (CD$_2$Cl$_2$): 221.40 (CO), 203.37 (NCN), 171.39 (NCO), 152.38, 137.71, 137.64, 137.11, 136.81, 134.91, 130.38, 129.33, 129.30, 129.18, 128.93, 128.76 (br), 127.71, 125.41, 114.12 (CC(Ru)C), 51.18 (NCCN), 20.96 (MesCH$_3$), 19.20 (MesCH$_3$), 19.15 (MesCH$_3$), 16.76 (br, XylCH$_3$).

IR(KBr): 1881 cm$^{-1}$ (vCO).

Anal. Calcd. for C$_{53}$H$_{55}$ClN$_4$O$_3$Ru (932.55): C, 68.26; H, 5.94; N, 6.01. Found: C, 68.22; H, 5.38; N, 5.83.

Synthesis of Cyclic Bent Allene Metal Complex 4—Ru(CBA)(PPh$_3$)(CO)H(OSO$_2$CF$_3$)

Halide exchange:

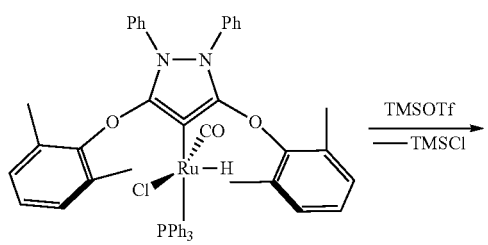

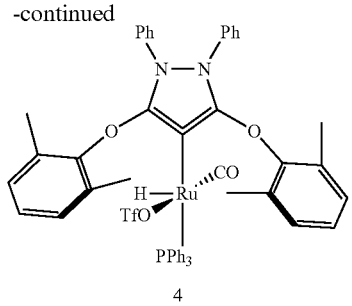

Employing silylated glassware, compound 2 (50 mg, 0.056 mmol) was dissolved in THF (2 mL) and Me$_3$SiOSO$_2$CF$_3$ (10.5 µL, 0.058 mmol) was added. Solvent was removed under high vacuum and yellow solid was washed with pentane (3×5 mL) and dried under high vacuum (54 mg, 96%). Small amounts (~5 mol-%) of in-separable [CBAH][OTf] are also observed due to acid impurities in commercially available Me$_3$SiOSO$_2$CF$_3$.

$^1$H-NMR (CD$_2$Cl$_2$): 7.60 (d, $^3J_{H-H}$=8.0 Hz, 4H, o-Ph), 7.52-7.38 (m, 15H, o-PPh$_3$, p-PPh$_3$, m-Ph & p-Ph), 7.30 (t, $^3J_{H-H}$=8.0 Hz, 6H, m-PPh$_3$), 7.09 (br s, 2H, m-OAr), 6.85 (br s, 2H, m-OAr), 6.16 (br s, 2H, p-OAr), 2.47 (br s, 6H, OArCH$_3$), 2.21 (br s, 6H, OArCH$_3$), −23.31 (d, $^2J_{H-P}$=23.3 Hz, 1H, RuH).

$^{13}$C-NMR (CD$_2$Cl$_2$): (Some signal overlap prevented unambiguous assignment). 204.53 (NCN), 158.84, 150.38, 135.40 (d, $^1J_{C-P}$=37.3 Hz, ipso-PPh$_3$), 134.19 (d, $^3J_{C-P}$=11.7 Hz, o-PPh$_3$), 133.80 (br), 132.42, 130.73, 130.32, 130.00, 129.80, 129.64, 129.62, 128.90, 128.11 (d, $^5J_{C-P}$=9.0 Hz, p-PPh$_3$), 103.05 (d, $^1J_{C-P}$=77.5 Hz, C$_{CBA}$), 17.20 (br, Me).

$^{19}$F-NMR(CD$_2$Cl$_2$): −78.67 (s) (OSO$_2$CF$_3$).

$^{31}$P-NMR(CD$_2$Cl$_2$): 43.16 (d, $^2J_{H-P}$=23.5 Hz, PPh$_3$).

IR(KBr): 1919 cm$^{-1}$ (vCO).

Anal. Calcd. for C$_{54}$H$_{55}$F$_3$ClN$_4$O$_6$PRuS (1002.01): C, 61.13; H, 4.43; N, 2.80. Found: C, 61.23; H, 4.84; N, 2.72.

Synthesis of Cyclic Bent Allene Metal Complex 5—Ru(CBA)(SIMes)(CO)H(OSO$_2$CF$_3$)

Halide exchange:

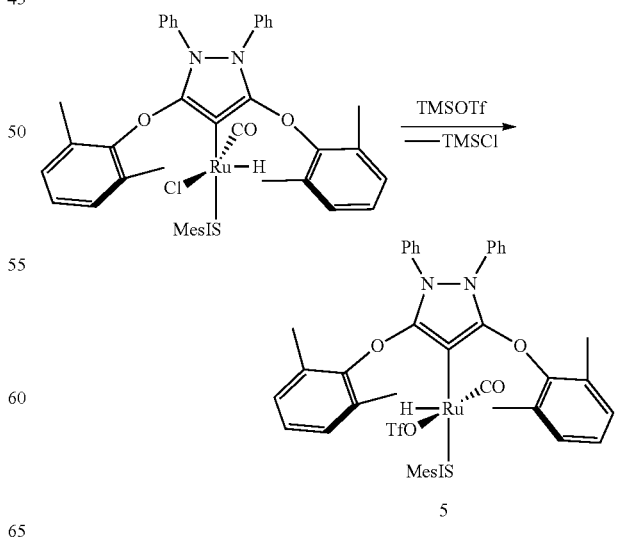

This was synthesized in an exactly analogous manner to 4 using compound 3. The product was obtained as an orange solid (87%). Small amounts (~5 mol %) of inseparable [CBAH][OTf] are also observed due to acid impurities in commercially available $Me_3SiOSO_2CF_3$.

$^1$H-NMR ($CD_2Cl_2$): 7.46-6.48 (br m, 20H, Ar), 3.90-3.73 (m, 4H, $NCH_2CH_2N$), 2.66-1.54 (br m, 24H, $ArCH_3$) 2.34 (s, 6H, $ArCH_3$), −26.56 (s, 1H, RuH).

$^{13}$C-NMR ($CD_2Cl_2$): Very broad low intensity signals are observed, select resonances are reported: 217.96 (CO), 205.83 (NCN), 137.41 (br), 131-128.5 (br m), 127.7 (br), 125.3 (br), 109.58 ($C_{CBA}$), 51.31 (br, NCCN), 20.85 (br, Me), 18.34 (br, Me), 18.14 (br, Me), 16.7 (br, Me).

$^{19}$F-NMR($CD_2Cl_2$): −77.91 (s) ($OSO_2CF_3$).

IR(KBr): 1886 cm$^{-1}$ (vCO).

Anal. Calcd. for $C_{54}H_{55}F_3ClN_4O_6RuS$ (1046.17): C, 62.00; H, 5.30; N, 5.36. Found: C, 62.02; H, 5.48; N, 5.14.

Cyclic bent allene metal complexes 3 and 5 are inventive examples while complexes 1, 2 and 4 (comprising $PPh_3$-ligands), are comparative examples.

Hydrogenation Procedures:

Hydrogenation procedure for Nitrile Butadiene Rubber: To 5.0 mL of a 5.0% w/w solution of NBR in chlorobenzene was added the appropriate complex (see catalyst loading in Table 2). The reactor was purged three times with 20 bar $H_2$ and was then filled with 45 bar of $H_2$. The temperature was adjusted to 80° C., and after a thermal equilibration period of 20 minutes, the pressure was adjusted to 50 bar $H_2$ and the reaction vessel was stirred magnetically for 20 hours. The reactor was then cooled to room temperature and the pressure was vented. The polymer was coagulated by the addition of methanol to the reaction vessel and stirred for a further 24 hours. The polymer was isolated by filtration, and dried under vacuum at 60° C. for 24 hours. The results are disclosed in Table 1.

Hydrogenation Procedure for Low Molecular Weight Olefins (Tables 1-5):

Under an inert atmosphere, of the appropriate complex (see catalyst loading in Tables 2-4) was weighed into a Parr vessel and dissolved in 1.0 mL $CH_2Cl_2$. 10 mmol of the appropriate substrate was the added, the vessel was sealed, and rapidly purged three times with 20 bar $H_2$. The vessel was then filled to 20 bar $H_2$ pressure and allowed to stir at ambient temperature. The pressure was vented after the allotted time, and the vessel was opened in air. The solution was filtered through silica, and conversion was determined by $^1$H-NMR or gas chromatography (GC). The results are disclosed in Tables 2-4.

TABLE 1

Hydrogenation of NBR using cyclic bent allene metal complexes 2-5. In all examples 5 mL of 5% w/w NBR in dry chlorobenzene; 50 bar $H_2$ pressure; 80° C.; 20 h.

| Complex | Complex loading [µmol] | [mg] | Degree of hydrogenation [%] | GPC of HNBR (1.0 mg/mL in THF) | | |
|---|---|---|---|---|---|---|
| | | | | $M_n$ | $M_w$ | PDI |
| 2 | 2.5 | 2.22 | Gel formed | — | — | — |
| | 0.5 | 0.44 | 0 | — | — | — |
| 3 | 2.5 | 2.33 | 100 | nd | nd | nd |
| | 0.5 | 0.47 | 100 | nd | nd | nd |
| | 0.2 | 0.187 | 100 | 110,000 | 259,000 | 2.35 |
| | 0.1 | 0.093 | 100 | 98,000 | 254,000 | 2.59 |
| | 0.05 | 0.047 | 100 | 97,000 | 248,000 | 2.56 |
| | 0.02 | 0.019 | 90 | 86,000 | 235,000 | 2.73 |
| | 0.01 | 0.009 | 57 | Polymer insoluble in THF | | |
| 4 | 2.5 | 2.50 | Gel formed | — | — | — |
| | 0.5 | 0.50 | Gel formed | — | — | — |
| 5 | 2.5 | 2.62 | 100 | nd | nd | nd |
| | 0.5 | 0.52 | 100 | nd | nd | nd |
| | 0.2 | 0.209 | 100 | 110,000 | 247,000 | 2.25 |
| | 0.1 | 0.104 | 100 | 101,000 | 235,000 | 2.33 |
| | 0.05 | 0.052 | 66 | 87,000 | 225,000 | 2.54 |

Complexes 3 and 5 resulted in 100% degree of hydrogenation.
Complexes 2 and 4 resulted in gel.
n.d. = not determined

TABLE 2

Hydrogenation of 1-hexene by cyclic bent allene metal complexes 2-5. In all examples 10 mmol 1-hexene in 1.00 mL $CH_2Cl_2$; 20 bar $H_2$; at 25° C.

| Complex | Complex loading [mol %] | Time [min] | Conversion to [%] 2-hexene | hexane | TON | TOF [h$^{-1}$] |
|---|---|---|---|---|---|---|
| 2 | 0.01 | 30 | 10 | 8 | 800 | 1,600 |
| 3 | 0.01 | 30 | 3 | 97 | 9,700 | 19,400 |
| 4 | 0.01 | 30 | 35 | 64 | 6,400 | 12,800 |
| 5 | 0.01 | 30 | 0 | 100 | 10,000 | 20,000 |
| | 0.01 | 15 | 0 | 100 | 10,000 | 40,000 |
| | 0.01 | 5 | 29 | 68 | 6,800 | 81,600 |
| | 0.005 | 30 | 6 | 92 | 18,400 | 36,800 |
| | 0.005 | 15 | 4 | 92 | 18,400 | 73,600 |
| | 0.005 | 5 | 18 | 47 | 9,400 | 112,800 |
| RuHCl(CO)(PCy$_3$)$_2$ | 0.01 | 30 | 2 | 79 | 7,900 | 15,800 |
| RuHCl(CO)(PPh$_3$)(SIMes) | 0.01 | 30 | 5 | 35 | 3,500 | 7,000 |

TABLE 3

Hydrogenation of cyclohexene by cyclic bent allene metal complexes 2-5. In all examples 10 mmol cyclohexene in 1.00 mL $CH_2CL_2$; 20 bar $H_2$; 25° C.

| Complex | Complex loading [mol %] | Time [min] | Conversion to cyclohexane [%] | TON | TOF [h$^{-1}$] |
|---|---|---|---|---|---|
| 2 | 0.05 | 30 | 0 | | |
| 3 | 0.05 | 30 | 11 | 220 | 440 |
| 4 | 0.05 | 30 | 6 | 120 | 240 |
| 5 | 0.05 | 30 | 100 | 2,000 | 4,000 |
| | 0.02 | 30 | 100 | 5,000 | 10,000 |
| | 0.02 | 15 | 71 | 3,550 | 14,200 |
| | 0.01 | 30 | 93 | 9,300 | 18,600 |
| | 0.005 | 30 | 7 | 1,400 | 2,800 |

TABLE 3-continued

Hydrogenation of cyclohexene by cyclic bent allene metal complexes 2-5. In all examples 10 mmol cyclohexene in 1.00 mL CH$_2$CL$_2$; 20 bar H$_2$; 25° C.

| Complex | Complex loading [mol %] | Time [min] | Conversion to cyclohexane [%] | TON | TOF [h$^{-1}$] |
|---|---|---|---|---|---|
| RuHCl(CO)(PCy$_3$)$_2$ | 0.05 | 30 | 0 | | |
| RuHCl(CO)(PPh$_3$)(SIMes) | 0.05 | 30 | <1 | | |
| RhCl(PPh$_3$)$_3$ | 0.05 | 30 | 18 | 360 | 720 |

TABLE 4

Hydrogenation of 2-methyl-2-butene by cyclic bent allene metal complex 5. In all examples 10 mmol 2-methyl-2-butene in 1.00 mL CH$_2$Cl$_2$ under 20 bar H$_2$ at 25° C.

| Complex | Complex loading mol [%] | Time [min] | Conversion to 2-methyl-butane [%] | TON | TOF [h$^{-1}$] |
|---|---|---|---|---|---|
| 5 | 0.1 | 60 | 100 | 1,000 | 1,000 |
| 5 | 0.1 | 30 | 91 | 910 | 1,820 |
| 5 | 0.05 | 120 | 100 | 2,000 | 1,000 |
| 5 | 0.05 | 30 | 56 | 1,120 | 2,240 |

TABLE 5

Hydrogenation of trans-β-methylstyrene by cyclic bent allene metal complex 5. In all examples 10 mmol trans-β-methylstyrene in 1.00 mL CH$_2$Cl$_2$ under 20 bar H$_2$ at 25° C.

| Complex | Complex loading [mol %] | Time [min] | Conversion to ethylbenzene [%] | TON | TOF [h$^{-1}$] |
|---|---|---|---|---|---|
| 5 | 0.05 | 30 | 88 | 1,760 | 3,520 |
| 5 | 0.05 | 60 | 95 | 1,900 | 1,900 |

Hydrogenation Procedure (Tables 6-11):

Under an inert atmosphere, catalyst was weighed into a Parr vessel and 3.0 mmol or 10 mmol of the appropriate substrate was added. The vessel was sealed, rapidly purged three times with 20 bar H$_2$, filled to 45 bar H$_2$ pressure, and placed in an 80° C. oil bath with rapid stirring for a thermal equilibration period of 15 minutes. After this time, pressure was adjusted to 50 bar, and the reactor was allowed to stir at this temperature for the allotted time. Upon completion, the reactor was allowed to cool to room temperature over a period of 30 minutes, the pressure was vented, and the vessel was opened in air. The contents were analyzed by $^1$H NMR and/or GC MS.

TABLE 6

Hydrogenation of dibutylitaconate by cyclic bent allene metal complex 5. In all examples 3 mmol neat dibutylitaconate under 50 bar H$_2$ at 80° C.

| Complex | Complex loading [mol %] | Time [h] | Conversion to Dibutyl methylsuccinate [%] | TON | TOF [h$^{-1}$] |
|---|---|---|---|---|---|
| 5 | 0.01 | 3 | 100 | 10,000 | 3,333 |
| 5 | 0.005 | 3 | 81 | 8,100 | 2,700 |

TABLE 7

Hydrogenation of isophorone by cyclic bent allene metal complex 5. In all examples 3 mmol neat isophorone under 50 bar H$_2$ at 80° C.

| Complex | Complex loading [mol %] | Time [h] | Conversion to 3,3,5-trimethylcyclohexanone [%] | TON | TOF [h$^{-1}$] |
|---|---|---|---|---|---|
| 5 | 0.001 | 3 | 94 | 94,000 | 31,333 |
| 5 | 0.0005 | 3 | 64 | 128,000 | 42,666 |

TABLE 8

Hydrogenation of 3-nitrostyrene by cyclic bent allene metal complex 5. In all examples 3 mmol neat 3-nitrostyrene under 50 bar H$_2$ at 80° C.

| Complex | Complex loading [mol %] | Time [h] | Conversion to 3-ethylnitrobenzene [%] | TON | TOF [h$^{-1}$] |
|---|---|---|---|---|---|
| 5 | 0.002 | 16 | 98 | 49,000 | 3,063 |

TABLE 9

Hydrogenation of terpinen-4-ol by cyclic bent allene metal complex 5. In all examples 10 mmol neat terpinen-4-ol under 50 bar H$_2$ at 80° C.

| Complex | Complex loading [mol %] | Time [h] | Conversion to trans-1-hydroxy-1-isopropyl-4-methylcyclohexane [%] | TON | TOF [h$^{-1}$] |
|---|---|---|---|---|---|
| 5 | 0.02 | 13 | 100 | 5,000 | 384 |
| 5 | 0.01 | 13 | 93 | 9,300 | 715 |

TABLE 10

Hydrogenation of 1-methyl-4-methoxy-4-isopropylcyclohexene by cyclic bent allene metal complex 5. In all examples 10 mmol neat 1-methyl-4-methoxy-4-isopropylcyclohexene under 50 bar H$_2$ at 80° C.

| Complex | Complex loading [mol %] | Time [h] | Conversion to trans-1-methoxy-1-isopropyl-4-methylcyclohexane [%] | TON | TOF [h$^{-1}$] |
|---|---|---|---|---|---|
| 5 | 0.05 | 2 | 95 | 1,900 | 950 |
| 5 | 0.02 | 2 | 72 | 3,600 | 1,800 |

The invention claimed is:

1. A cyclic bent allene metal complex of the general formula (I)

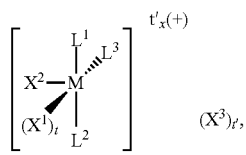

(I)

wherein
M is a transition metal selected from Groups 6-11 of the periodic table,
$L^1$ is a cyclic bent allene ligand according to the general formula (II)

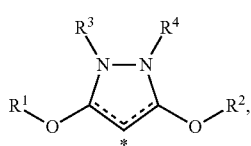

(II)

wherein each of $R^1$, $R^2$, $R^3$ and $R^4$ is independently selected from the group consisting of $C_1$-$C_{10}$-alkyl, $C_3$-$C_{10}$-cycloalkyl, $C_2$-$C_{10}$-alanyl, $C_3$-$C_{10}$-cycloalkenyl, $C_2$-$C_{10}$-alkynyl, $C_6$-$C_{24}$-aryl, $C_2$-$C_{20}$-heteroaryl, $C_1$-$C_{10}$-heteroalkyl, $C_2$-$C_{10}$-heterocycloalkyl, $C_1$-$C_{10}$-alkoxy, $C_2$-$C_{10}$-alkenyloxy, $C_2$-$C_{10}$-alkynyloxy, halogen, $C_6$-$C_{24}$-aryloxy, $C_2$-$C_{20}$-heteroaryloxy, $C_2$-$C_{10}$-alkoxycarbonyl, $C_1$-$C_{10}$-alkylthio, $C_2$-$C_{10}$-alkenylthio, $C_2$-$C_{10}$-alkynylthio, $C_1$-$C_{10}$-alkylsulfonyl, $C_1$-$C_{10}$-alkylsulfinyl, $C_6$-$C_{24}$-arylsulfonyl, $C_6$-$C_{24}$-aryl-$C_1$-$C_{10}$-alkyl, $C_2$-$C_{20}$-heteroaryl-$C_1$-$C_{10}$-alkyl, $C_6$-$C_{24}$-aryl-$C_1$-$C_{10}$-heteroalkyl, $C_2$-$C_{20}$-heteroaryl-$C_1$-$C_{10}$-heteroalkyl, amino, amido, alkylamino, a phosphorus comprising group, a silicon comprising group and a boron comprising group, and
wherein the (*) indicates the binding site to the metal M,
$L^2$ is an NHC-ligand,
$L^3$ is a π-acidic donor ligand,
$X^1$ is an anionic ligand,
$X^2$ is hydride,
$X^3$ is a non-coordinating anion,
t is either 0 or 1, and
t' is either 0 or 1, wherein t and t' may not both represent 0 at the same time.

2. The complex according to claim 1, wherein:
M is a transition metal selected from a group consisting of ruthenium, rhodium, palladium, osmium, iridium and platinum,
$L^1$ is a cyclic bent allene ligand represented by formula (a), wherein $R^1$ and $R^2$ of the formula (II) are independently butyl, phenyl, 2,4,6-trimethylphenyl, 2,6-diisopropylphenyl or 2,6-dimethylphenyl and $R^3$ and $R^4$ are independently hydrogen, butyl, phenyl, 2,4,6-trimethylphenyl, 2,6-diisopropylphenyl or 2,6-dimethylphenyl, $L^2$ is an NHC-ligand of the general formula (IIa) to (IIe)

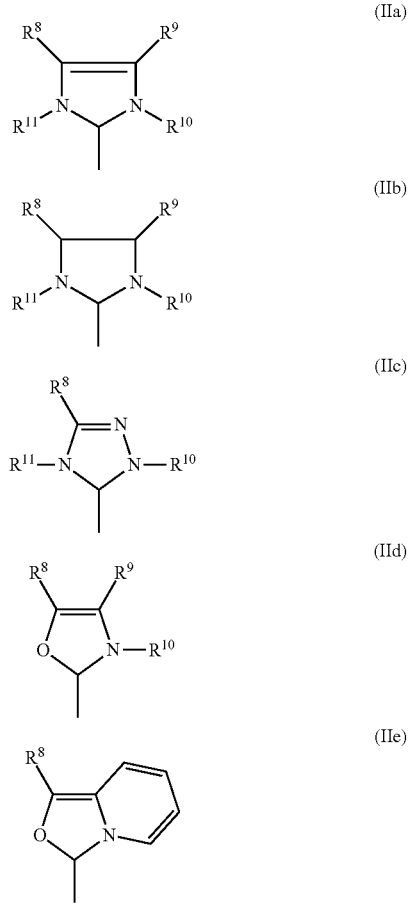

wherein
$R^8$ and R are identical or different and represent hydrogen, $C_6$-$C_{24}$-aryl, straight-chain or branched $C_1$-$C_{10}$-alkyl, or form a cycloalkyl or aryl structure together with the carbon atoms to which they are bound, and
$R^{10}$ and $R^{11}$ are identical or different and preferably represent straight-chain or branched $C_1$-$C_{10}$-alkyl, $C_3$-$C_{10}$-cycloalkyl, substituted or unsubstituted $C_6$-$C_{24}$-aryl, $C_1$-$C_{10}$-alkylsulfonate, or $C_6$-$C_{24}$-arylsulfonate,
$L^3$ is carbonyl (CO), nitrosyl (NO) or isocyanide,
$X^1$ is hydride, fluorine, chlorine, bromine or iodine, cyanide, thiocyanate, cyanate, isocyanate, isothiocyanate, phosphate, borate, carboxylate, acetate ($CH_3COO$), trifluoroacetate ($CF_3COO$), $CFH_2COO$, $(CH_3)_3CO$, $(CF_3)_2(CH_3)CO$, $(CF_3)(CH_3)_2CO$, trifluormethylsulfonate (abbreviated -OTf; $CF_3SO_3$), tosylate (p-$CH_3$—$C_6H_4$—$SO_3$), mesylate ($CH_3SO_3$) benzoate, $C_1$-$C_5$-carboxylate, $C_1$-$C_5$-alkyl, phenoxy, $C_1$-$C_5$-alkoxy, $C_1$-$C_5$-alkylthiol, $C_6$-$C_{24}$-arylthiol, $C_6$-$C_{24}$-aryl- or $C_1$-$C_5$-alkylsulfonate,
$X^2$ is hydride, and
$X^3$, t and t' have the meanings outlined for general formula (I).

3. The complex according to claim 1, wherein:
M is ruthenium or osmium,
$L^1$ is a cyclic bent allene ligand represented by formula (II) wherein $R^1$ and $R^2$ of the formula (II) are independently butyl, phenyl, 2,4,6-trimethylphenyl, 2,6-diisopropylphenyl or 2,6-dimethylphenyl and $R^3$ and $R^4$ are independently hydrogen, butyl or phenyl, $L^2$ is an NHC-ligand of the general formula (IIa) to (IIe)

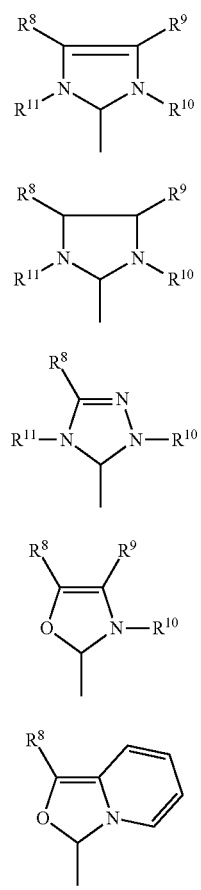

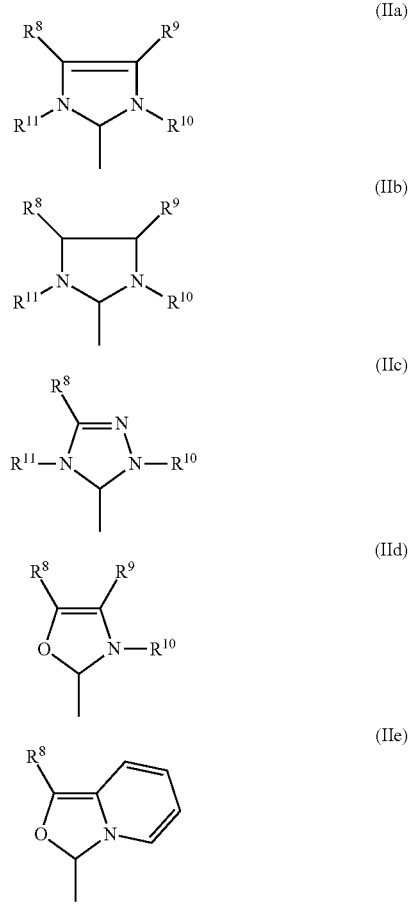

wherein
- $R^8$ and $R^9$ are identical or different and represent hydrogen, $C_6$-$C_{24}$-aryl, straight-chain or branched $C_1$-$C_{10}$-alkyl, or form a cycloalkyl or aryl structure together with the carbon atoms to which they are bound, and
- $R^{10}$ and $R^{11}$ are identical or different and preferably represent straight-chain or branched $C_1$-$C_{10}$-alkyl, $C_3$-$C_{10}$-cycloalkyl, substituted or unsubstituted $C_6$-$C_{24}$-aryl, $C_1$-$C_{10}$-alkylsulfonate, or $C_6$-$C_{24}$-arylsulfonate, $L^3$ is carbonyl (CO) or nitrosyl (NO),
$X^1$ is trifluormethylsulfonate ($CF_3SO_3$) or chloride,
$X^2$ is hydride, and
$X^3$, t and t' have the meanings outlined for general formula (I).

4. The complex according to claim 1, wherein:
M is ruthenium,
$L^1$ is a cyclic bent allene ligand of general formula (II) wherein $R^1$ and $R^2$ of the formula (II) are phenyl and $R^3$ and $R^4$ are 2,6-dimethyl-phenyl,
$L^2$ is an NHC-ligand of the general formula (IIa) to (IIe)

wherein
$R^8$ and $R^9$ are hydrogen, and
$R^{10}$ and $R^{11}$ are 2,4,6-trimethylphenyl (Mes),
$L^3$ is carbonyl (CO),
$X^1$ is chloride,
$X^2$ is hydride, and
$X^3$, t and t' have the meanings outlined for general formula (I).

5. A process for preparing hydrogenated olefins, preferably terminal, internal, cyclic or conjugated olefins, the process comprising hydrogenating the olefin in the presence of at least one complex of general formula (I) according to claim 1.

6. A process for preparing partially or fully hydrogenated nitrile rubbers, the process comprising hydrogenating a nitrile rubber in the presence of at least one complex of general formula (I) according to claim 1.

7. The process according to claim 6, further comprising conducting the hydrogenation at a temperature of 0° C. to 200° C., preferably from 15° C. to 150° C., and at a hydrogen pressure of 0.1 MPa to 20 MPa, preferably of 1 MPa to 16 MPa.

8. The process according to claim 6, wherein the amount of the complex to the nitrile rubber is 0.000001 phr to 0.5 phr, based on the nitrile rubber used.

9. The process according to claim 6, wherein the nitrile rubber is a copolymer or terpolymer comprising repeating units of:

(i) at least one α,β-unsaturated nitrile, preferably at least one $C_3$-$C_5$-α,β-unsaturated nitrile, more preferably selected from the group consisting of acrylonitrile, methacrylonitrile, ethacrylonitrile and mixtures thereof, and most preferably acrylonitrile,
(ii) at least one conjugated diene, preferably at least one $C_4$-$C_6$-conjugated diene, more preferably selected from the group consisting of 1,3-butadiene, isoprene, 2,3-dimethylbutadiene, piperylene and mixtures thereof, most preferably 1,3-butadiene, and
(iii) optionally one or more further copolymerizable monomers selected from the group consisting of α,β-unsaturated, preferably mono-unsaturated, monocarboxylic acids, their esters and amides, α,β-unsaturated, preferably mono-unsaturated, dicarboxylic acids, their mono- or diesters and the respective anhydrides or amides of said α,β-unsaturated dicarboxylic acids.

10. A method for the hydrogenation of unsaturated compounds comprising carbon-carbon double bonds, the method comprising contacting the unsaturated compounds with a catalyst comprising the complex of general formula (I) according to claim 1.

* * * * *